United States Patent [19]
Hill

[11] Patent Number: 5,941,894
[45] Date of Patent: *Aug. 24, 1999

[54] BLOOD VESSEL OCCLUSION DEVICE

[75] Inventor: John Donald Hill, San Fransisco, Calif.

[73] Assignee: Heartport, Inc., Redwood City, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/896,494

[22] Filed: Jul. 18, 1997

Related U.S. Application Data

[63] Continuation of application No. 08/714,887, Sep. 17, 1996, which is a continuation-in-part of application No. 08/479,408, Jun. 7, 1995, Pat. No. 5,556,412, which is a division of application No. 08/209,280, Mar. 14, 1994, Pat. No. 5,499,996, which is a division of application No. 07/808,767, Dec. 17, 1991, Pat. No. 5,330,498.

[51] Int. Cl.$^6$ .................................................. A61B 17/00
[52] U.S. Cl. ............................................. 606/194; 604/96
[58] Field of Search ........................... 606/194, 191–193; 604/96–104, 51–53

[56] References Cited

U.S. PATENT DOCUMENTS 2,854,982  10/1958  Pagano .
3,039,468   6/1962  Price .

(List continued on next page.)

FOREIGN PATENT DOCUMENTS

| 0121667 | 10/1984 | European Pat. Off. . |
| 0 335 205 | 1/1985 | European Pat. Off. . |
| 0 161 045 | 11/1985 | European Pat. Off. . |
| 0218275 | 4/1987 | European Pat. Off. . |
| 0 249 338 | 5/1987 | European Pat. Off. . |

(List continued on next page.)

OTHER PUBLICATIONS

Buckberg, "Strategies and Logic of Cardioplegic Delivery to Prevent, Avoid, and Reverse Ischemmic and Reperfusion Damage," *J Thorac Vasc Surg,* 1987;93:127–129.

Cosgrove, "Management of the Calcified Aorta: An alternative method of occlusion," *Ann Thorac Surg* 1983;36:718–719.

DLP, Inc., Directions for Use: Cardioplegic Pressure Cannula with Vent Line, Code #14009 9 Gauge (No date).

Erath and Stoney, "Balloon Catheter Occlusion of the Ascending Aorta," *Ann Thorac Surg* , 1983;35:560–561.

Farcot et al., "New Catheter–pump System for Diastolic Synchronized Coronary Sinus Retroperfusion (D.S.R.)," *Med Prog Technol,* 1980;8(1):29–37.

Foster and Threlkel, "Proximal Control of Aorta with a Ballon Catheter," *Surg Gynecology & Obstetrics,* 1971, pp. 693–694.

(List continued on next page.)

*Primary Examiner*—Michael Buiz
*Assistant Examiner*—Vikki Trinh
*Attorney, Agent, or Firm*—Baker & Botts, L.L.P.

[57] ABSTRACT

An occluder apparatus for obstructing the flow of blood in a blood vessel has an elongated hollow tubular body having a leading end sized for reception in the blood vessel and includes portion of the body fabricated from a material soluble in blood, and a piercing device for inserting the body through the wall of the blood vessel to extend the leading end into the interior of the blood vessel. An inflatable diaphragm is carried by the body in a collapsed, deflated condition, and the apparatus includes a passage for conducting an inflating fluid from an external source, which is into fluid communication with the interior of the diaphragm, to effect expansion the diaphragm. Elongated openings in the body enable the diaphragm to be released in an inflated state from the body into flexible occluding engagement with the interior wall of the blood vessel about the full circumference of a transverse section thereof.

10 Claims, 15 Drawing Sheets

U.S. PATENT DOCUMENTS

| | | |
|---|---|---|
| 3,244,172 | 4/1966 | Brown . |
| 3,385,300 | 5/1968 | Holter . |
| 3,448,739 | 6/1969 | Stark et al. . |
| 3,548,805 | 12/1970 | Datsenko . |
| 3,675,656 | 7/1972 | Hakim . |
| 3,717,151 | 2/1973 | Collett . |
| 3,730,186 | 5/1973 | Edmunds, Jr. et al. . |
| 3,736,939 | 6/1973 | Taylor . |
| 3,769,960 | 11/1973 | Robinson . |
| 3,788,328 | 1/1974 | Alley et al. . |
| 3,789,852 | 2/1974 | Kim et al. . |
| 3,795,246 | 3/1974 | Sturgeon . |
| 3,833,003 | 9/1974 | Taricco . |
| 3,837,347 | 9/1974 | Tower . |
| 3,889,686 | 6/1975 | Duturbure . |
| 3,903,895 | 9/1975 | Alley et al. . |
| 3,915,171 | 10/1975 | Shermeta . |
| 3,952,742 | 4/1976 | Taylor . |
| 3,989,049 | 11/1976 | Yoon . |
| 4,122,858 | 10/1978 | Schiff . |
| 4,154,227 | 5/1979 | Krause et al. . |
| 4,173,981 | 11/1979 | Mortensen et al. . |
| 4,180,068 | 12/1979 | Jacobsen et al. . |
| 4,240,433 | 12/1980 | Bordow . |
| 4,248,224 | 2/1981 | Jones . |
| 4,256,094 | 3/1981 | Kapp et al. . |
| 4,284,073 | 8/1981 | Krause et al. . |
| 4,285,341 | 8/1981 | Pollack . |
| 4,287,892 | 9/1981 | Schiff . |
| 4,292,970 | 10/1981 | Hession, Jr. . |
| 4,323,071 | 4/1982 | Simpson et al. . |
| 4,327,709 | 5/1982 | Hanson et al. . |
| 4,328,056 | 5/1982 | Snooks . |
| 4,328,806 | 5/1982 | Cooper . |
| 4,411,653 | 10/1983 | Razi . |
| 4,413,989 | 11/1983 | Schjeldahl et al. . |
| 4,417,576 | 11/1983 | Baran . |
| 4,430,081 | 2/1984 | Timmermans . |
| 4,439,186 | 3/1984 | Kuhl . |
| 4,456,000 | 6/1984 | Schjeldahl et al. . |
| 4,459,977 | 7/1984 | Pizon . |
| 4,493,697 | 1/1985 | Krause et al. . |
| 4,496,345 | 1/1985 | Hasson . |
| 4,512,762 | 4/1985 | Spears . |
| 4,517,979 | 5/1985 | Pecenka . |
| 4,527,549 | 7/1985 | Gabbay . |
| 4,531,519 | 7/1985 | Dunn et al. . |
| 4,531,935 | 7/1985 | Berryessa . |
| 4,531,936 | 7/1985 | Gordon . |
| 4,535,757 | 8/1985 | Webster, Jr. . |
| 4,535,773 | 8/1985 | Yoon . |
| 4,540,399 | 9/1985 | Litzie et al. . |
| 4,542,743 | 9/1985 | Dunn et al. . |
| 4,552,558 | 11/1985 | Muto . |
| 4,559,041 | 12/1985 | Razi . |
| 4,571,241 | 2/1986 | Christopher . |
| 4,573,966 | 3/1986 | Weikl et al. . |
| 4,592,340 | 6/1986 | Boyles . |
| 4,596,552 | 6/1986 | DeVries . |
| 4,601,706 | 7/1986 | Aillón . |
| 4,601,713 | 7/1986 | Fuqua . |
| 4,610,662 | 9/1986 | Weikl et al. . |
| 4,627,837 | 12/1986 | Gonzalo . |
| 4,636,195 | 1/1987 | Wolinsky . |
| 4,648,384 | 3/1987 | Schmukler . |
| 4,655,752 | 4/1987 | Honkanen et al. . |
| 4,664,125 | 5/1987 | Pinto . |
| 4,676,778 | 6/1987 | Nelson, Jr. . |
| 4,681,117 | 7/1987 | Brodman et al. . |
| 4,689,041 | 8/1987 | Corday et al. . |
| 4,692,148 | 9/1987 | Kantrowitz et al. . |
| 4,697,574 | 10/1987 | Karcher et al. . |
| 4,705,507 | 11/1987 | Boyles . |
| 4,712,551 | 12/1987 | Rayhanabad . |
| 4,714,460 | 12/1987 | Calderon . |
| 4,722,347 | 2/1988 | Abrams et al. . |
| 4,723,550 | 2/1988 | Bales et al. . |
| 4,741,328 | 5/1988 | Gabbay . |
| 4,751,924 | 6/1988 | Hammerschmidt et al. . |
| 4,753,637 | 6/1988 | Horneffer . |
| 4,771,777 | 9/1988 | Horzewski et al. . |
| 4,777,951 | 10/1988 | Cribier et al. . |
| 4,779,611 | 10/1988 | Grooters et al. . |
| 4,785,795 | 11/1988 | Singh . |
| 4,790,825 | 12/1988 | Bernstein et al. . |
| 4,794,928 | 1/1989 | Kletschka . |
| 4,798,588 | 1/1989 | Aillon . |
| 4,802,479 | 2/1989 | Haber et al. . |
| 4,809,681 | 3/1989 | Kantrowitz et al. . |
| 4,820,271 | 4/1989 | Deutsch . |
| 4,828,544 | 5/1989 | Lane et al. . |
| 4,850,969 | 7/1989 | Jackson . |
| 4,861,334 | 8/1989 | Nawaz . |
| 4,877,031 | 10/1989 | Conway et al. . |
| 4,877,035 | 10/1989 | Bogen et al. . |
| 4,881,939 | 11/1989 | Newman . |
| 4,886,507 | 12/1989 | Patton et al. . |
| 4,889,137 | 12/1989 | Kolobow . |
| 4,898,168 | 2/1990 | Yule . |
| 4,902,272 | 2/1990 | Milder et al. . |
| 4,917,667 | 4/1990 | Jackson . |
| 4,919,651 | 4/1990 | Doane . |
| 4,921,484 | 5/1990 | Hillstead . |
| 4,927,412 | 5/1990 | Menasche . |
| 4,934,996 | 6/1990 | Mohl et al . |
| 4,943,275 | 7/1990 | Stricker . |
| 4,943,277 | 7/1990 | Bolling . |
| 4,946,440 | 8/1990 | Hall . |
| 4,960,412 | 10/1990 | Fink . |
| 4,966,604 | 10/1990 | Reiss . |
| 4,969,470 | 11/1990 | Mohl et al. . |
| 4,979,939 | 12/1990 | Shiber . |
| 4,985,014 | 1/1991 | Orejola . |
| 4,994,033 | 2/1991 | Shockey et al. . |
| 5,007,896 | 4/1991 | Shiber . |
| 5,009,636 | 4/1991 | Wortley et al. . |
| 5,011,468 | 4/1991 | Lundquist et al. . |
| 5,011,469 | 4/1991 | Buckberg et al. . |
| 5,011,488 | 4/1991 | Ginsburg . |
| 5,013,296 | 5/1991 | Buckberg et al. . |
| 5,021,044 | 6/1991 | Sharkaway . |
| 5,021,045 | 6/1991 | Buckberg et al. . |
| 5,024,688 | 6/1991 | Peters et al. . |
| 5,026,366 | 6/1991 | Leckrone . |
| 5,033,998 | 7/1991 | Corday et al. . |
| 5,041,093 | 8/1991 | Chu . |
| 5,041,098 | 8/1991 | Loiterman et al. . |
| 5,046,503 | 9/1991 | Schneiderman . |
| 5,047,041 | 9/1991 | Samuels . |
| 5,049,132 | 9/1991 | Shaffer et al. . |
| 5,053,008 | 10/1991 | Bajaj . |
| 5,059,167 | 10/1991 | Lundquist et al. . |
| 5,059,177 | 10/1991 | Towne et al. . |
| 5,069,661 | 12/1991 | Trudell . |
| 5,069,662 | 12/1991 | Bodden . |
| 5,071,405 | 12/1991 | Piontek et al. . |
| 5,090,960 | 2/1992 | Don Michael . |
| 5,106,368 | 4/1992 | Uldall et al. . |
| 5,109,859 | 5/1992 | Jenkins . |
| 5,112,305 | 5/1992 | Barath et al. . |
| 5,116,305 | 5/1992 | Milder et al. . |
| 5,122,122 | 6/1992 | Allgood . |

| | | |
|---|---|---|
| 5,125,903 | 6/1992 | McLaughlin et al. . |
| 5,135,474 | 8/1992 | Swan et al. . |
| 5,147,377 | 9/1992 | Sahota . |
| 5,152,754 | 10/1992 | Plyley et al. . |
| 5,152,771 | 10/1992 | Sabbaghian et al. . |
| 5,167,628 | 12/1992 | Boyles . |
| 5,171,232 | 12/1992 | Castillo et al. . |
| 5,176,619 | 1/1993 | Segalowitz . |
| 5,176,647 | 1/1993 | Knoepfler . |
| 5,186,713 | 2/1993 | Raible . |
| 5,195,942 | 3/1993 | Weil et al. . |
| 5,197,952 | 3/1993 | Marcadis et al. . |
| 5,203,773 | 4/1993 | Green . |
| 5,209,741 | 5/1993 | Spaeth . |
| 5,216,032 | 6/1993 | Manning . |
| 5,219,326 | 6/1993 | Hattler . |
| 5,226,427 | 7/1993 | Buckberg et al. . |
| 5,236,413 | 8/1993 | Feiring . |
| 5,246,424 | 9/1993 | Wilk . |
| 5,250,069 | 10/1993 | Nobuyoshi et al. . |
| 5,256,147 | 10/1993 | Vidal et al. . |
| 5,256,149 | 10/1993 | Banik et al. . |
| 5,275,622 | 1/1994 | Lazarus et al. . |
| 5,279,567 | 1/1994 | Ciaglia et al. . |
| 5,290,231 | 3/1994 | Marcadis et al. . |
| 5,290,249 | 3/1994 | Foster et al. . |
| 5,295,958 | 3/1994 | Shturman . |
| 5,308,320 | 5/1994 | Safar . |
| 5,312,344 | 5/1994 | Grinfeld et al. . |
| 5,312,361 | 5/1994 | Zadini et al. . |
| 5,314,418 | 5/1994 | Takano et al. . |
| 5,318,532 | 6/1994 | Frassica . |
| 5,322,509 | 6/1994 | Rickerd . |
| 5,324,268 | 6/1994 | Yoon . |
| 5,330,497 | 7/1994 | Freitas et al. . |
| 5,330,498 | 7/1994 | Hill . |
| 5,334,142 | 8/1994 | Paradis . |
| 5,338,305 | 8/1994 | Plyley et al. . |
| 5,350,393 | 9/1994 | Yoon . |
| 5,352,206 | 10/1994 | Cushieri et al. . |
| 5,354,270 | 10/1994 | Wilk et al. . |
| 5,356,421 | 10/1994 | Castro . |
| 5,366,445 | 11/1994 | Haber et al. . |
| 5,368,607 | 11/1994 | Freitas . |
| 5,370,625 | 12/1994 | Shichman . |
| 5,374,245 | 12/1994 | Mahurkar . |
| 5,380,282 | 1/1995 | Burns . |
| 5,383,854 | 1/1995 | Safar et al. . |
| 5,395,330 | 3/1995 | Marcadis et al. . |
| 5,397,306 | 3/1995 | Nobuyoshi et al. . |
| 5,411,479 | 5/1995 | Bodden . |
| 5,425,708 | 6/1995 | Nasu . |
| 5,433,446 | 7/1995 | Shturman . |
| 5,433,700 | 7/1995 | Peters . |
| 5,439,443 | 8/1995 | Miyata et al. . |
| 5,499,996 | 3/1996 | Hill . |
| 5,509,897 | 4/1996 | Twardowski et al. . |
| 5,522,838 | 6/1996 | Hill . |
| 5,527,292 | 6/1996 | Adams et al. . |
| 5,549,595 | 8/1996 | Freitas . |
| 5,556,412 | 9/1996 | Hill . |
| 5,569,293 | 10/1996 | Yoon . |
| 5,599,329 | 2/1997 | Gabbay . |
| 5,607,439 | 3/1997 | Yoon . |

FOREIGN PATENT DOCUMENTS

| | | |
|---|---|---|
| 0 238 106 | 9/1987 | European Pat. Off. . |
| 0 277 367 | 8/1988 | European Pat. Off. . |
| 0 321 614 | 6/1989 | European Pat. Off. . |
| 0 414 350 | 6/1990 | European Pat. Off. . |
| 0609914 | 8/1994 | European Pat. Off. . |
| 2246526 | 3/1973 | Germany . |
| 334404 | 1/1936 | Italy . |
| 1371701 | 2/1988 | U.S.S.R. . |
| 1 097 882 | 3/1965 | United Kingdom . |
| 1097881 | 3/1965 | United Kingdom . |
| 1284701 | 4/1971 | United Kingdom . |
| 1414344 | 5/1973 | United Kingdom . |
| 1467976 | 3/1974 | United Kingdom . |
| 1477665 | 4/1974 | United Kingdom . |
| 1513918 | 8/1975 | United Kingdom . |
| WO 81/03613 | 12/1981 | WIPO . |
| WO 83/03204 | 9/1983 | WIPO . |
| WO 89/10155 | 11/1989 | WIPO . |
| WO 91/01689 | 2/1991 | WIPO . |
| WO 91/08791 | 6/1991 | WIPO . |
| WO 91/10456 | 7/1991 | WIPO . |
| WO 92/17118 | 10/1992 | WIPO . |
| WO 93/07927 | 4/1993 | WIPO . |

OTHER PUBLICATIONS

Medi–Tech, Boston Scientific Corporation, "Occlusion Balloon Catheters: Instructions for Use," Rev. Jun., 1991.

Medtronic Bio–Medicus, Inc. "Bio–Medicus Cannula Instructions for Use Manual, Sterile and Non–Pyrogenic Single–Use Only," PN 885281 Rev. C(Oct. 1991).

Medtronic Bio–Medicus, Inc. "Bio–Medicus Cannula Introducer Instructions for Use Manual," PN 85146–Rev. C(Jul. 1991).

Meerbaum et al., "Diastolic Retroperfusion of Acutely Ischemic Myocardium," *Am J Cardiol,* 1976;37:588–598.

Meerbaum et al., "Hypothermic Coronary Venous Phased Retroperfusion: A Closed–Chest Treatment of Acute Regional Myocardial Ishcmeia," *Circulation,* 1982;65(7):1435–1445.

Rossi, "Long–term Cardiopulmonary Bypass by Peripheral Cannulation in a Model of Total Heart Failure," *J Thorac Card Vasc Surg,* 1990;914–921.

Uchida et al., "Percutaneous Fiberoptic Angioscopy of the Cardiac Valves," *Am Heart J,* 1991;121(6 partI): 1791–1798.

Yamaguchi, "A Case of Reoperation Using a Balloon Catheter with Blocked Pars Ascendes Aortae," *Kyobu Geka,* 1991;421(11):961–964.

Cardiovascular Research, Inc., *The Cannula Introducer* (No date).

International Search Report mailed Jul. 11, 1997.

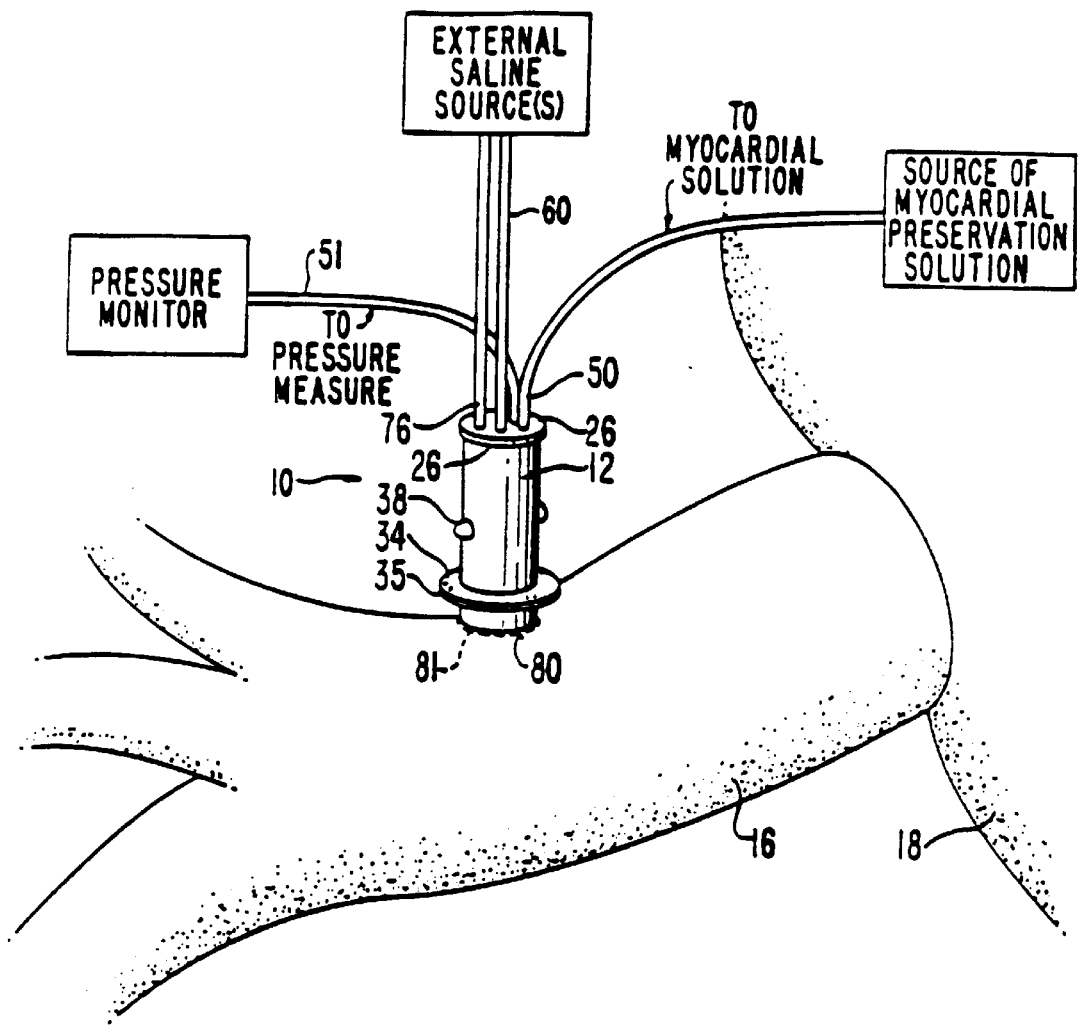

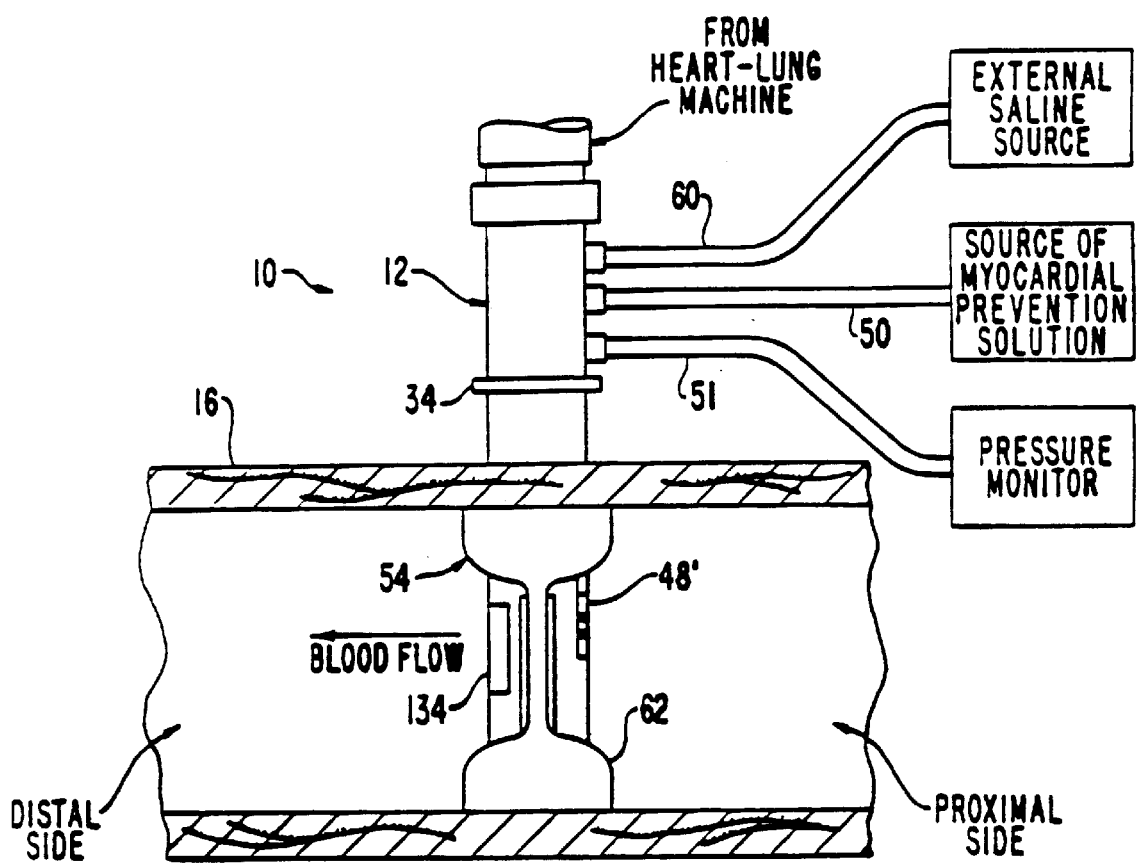

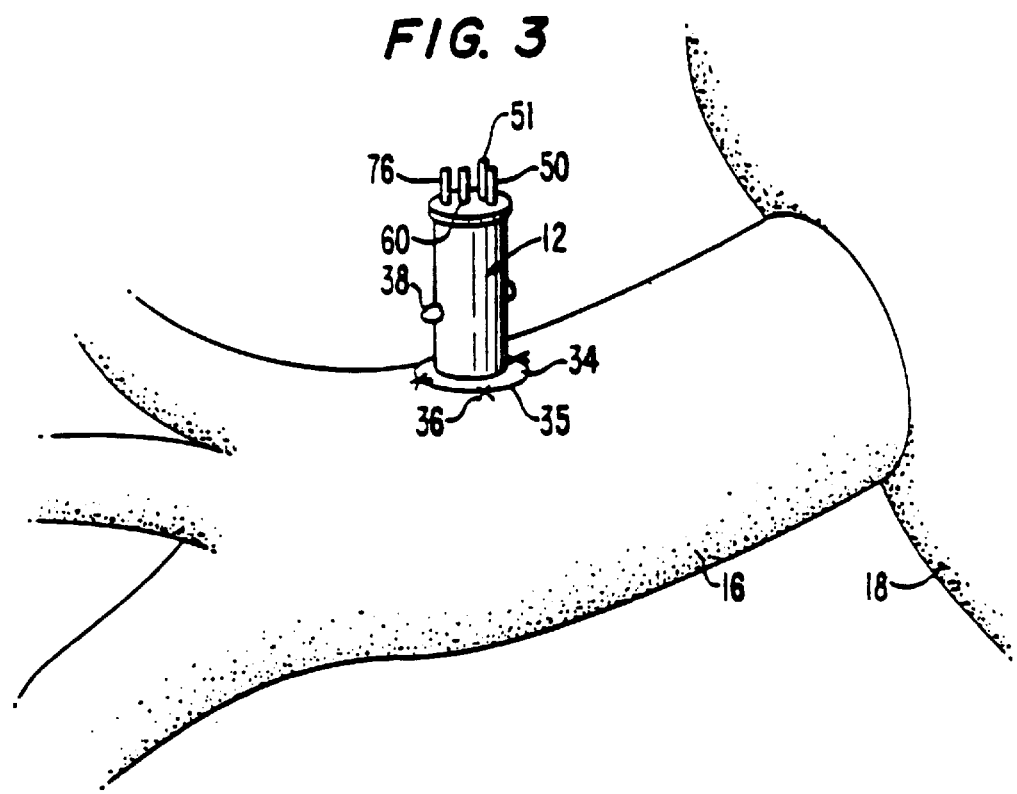

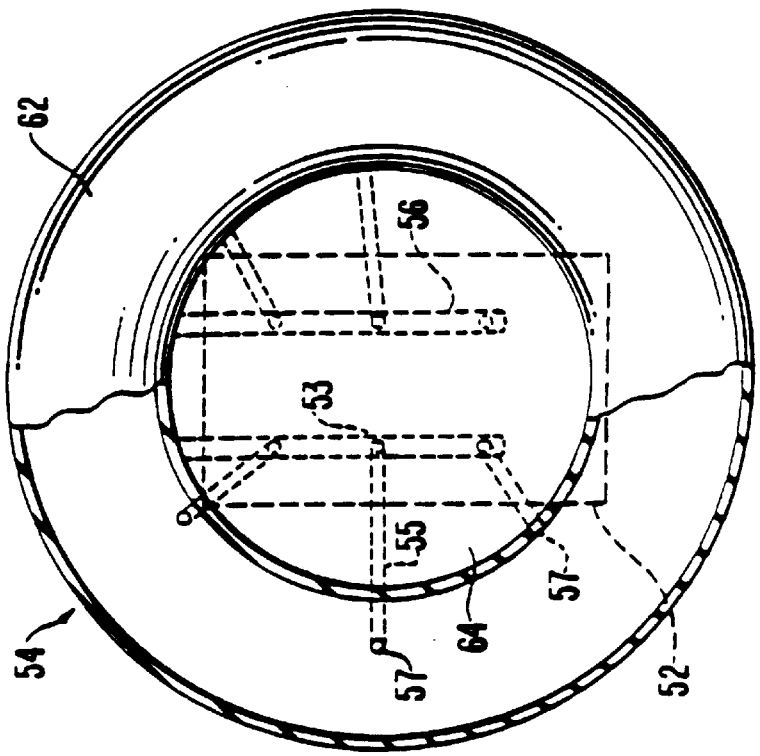
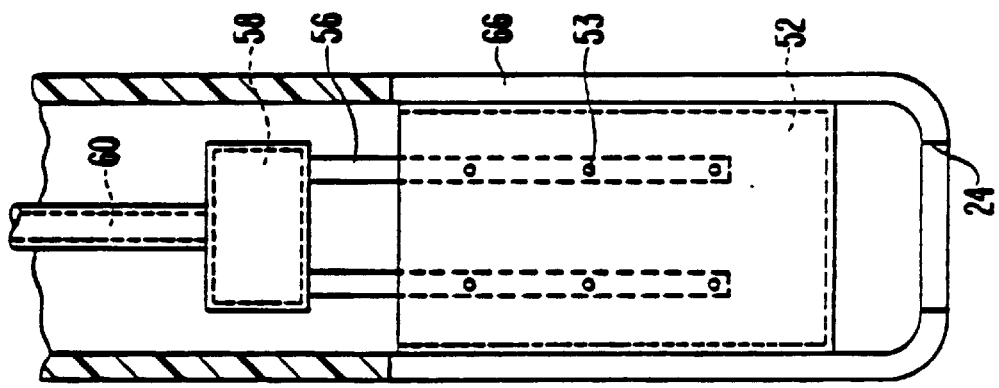

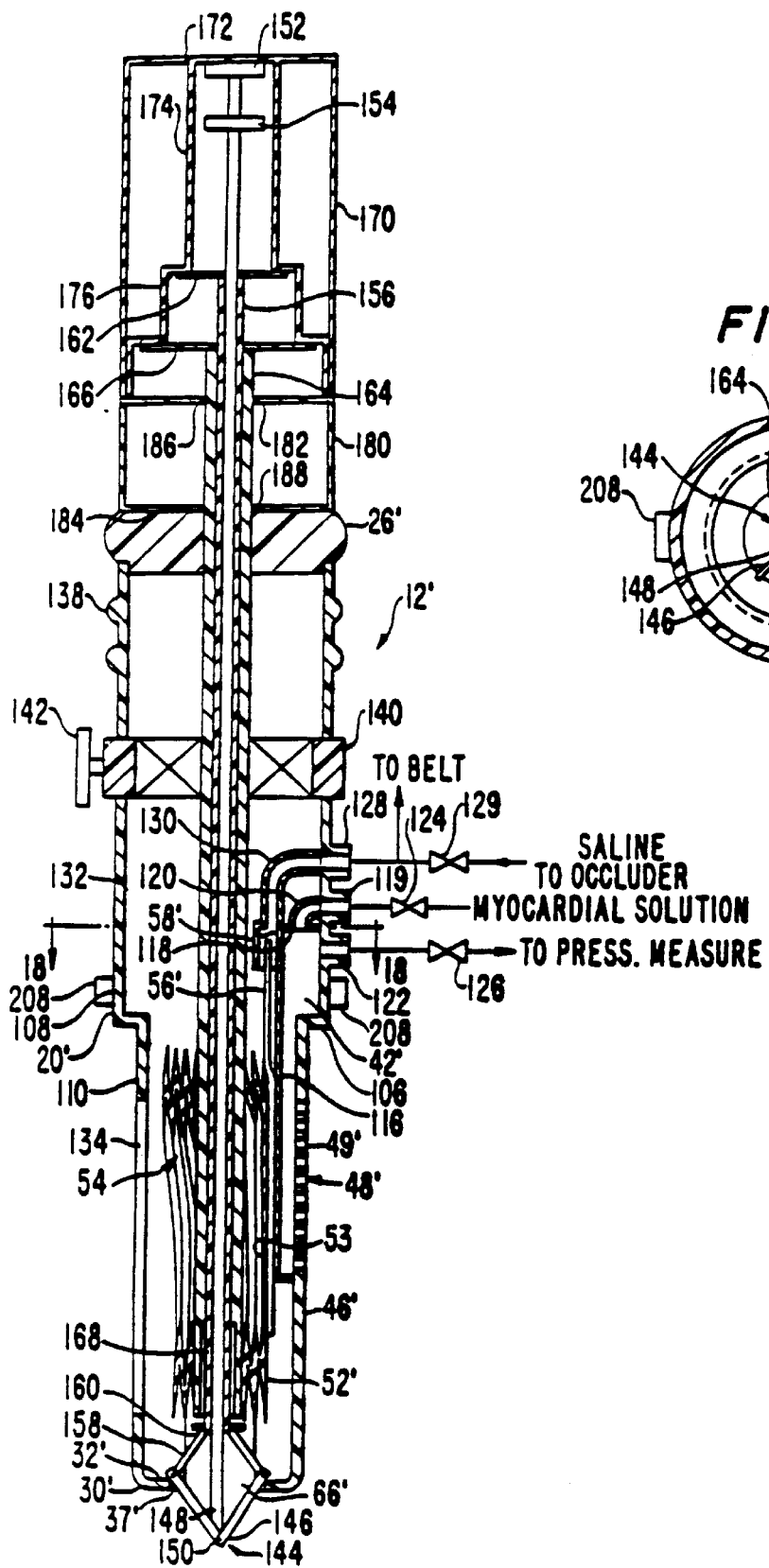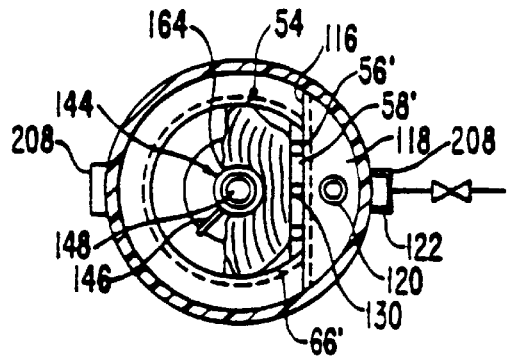

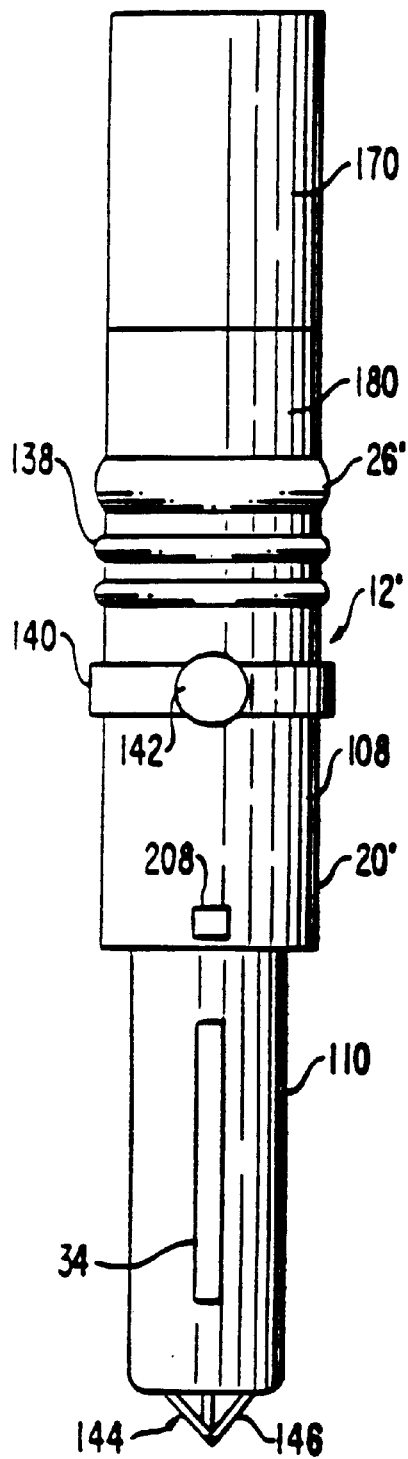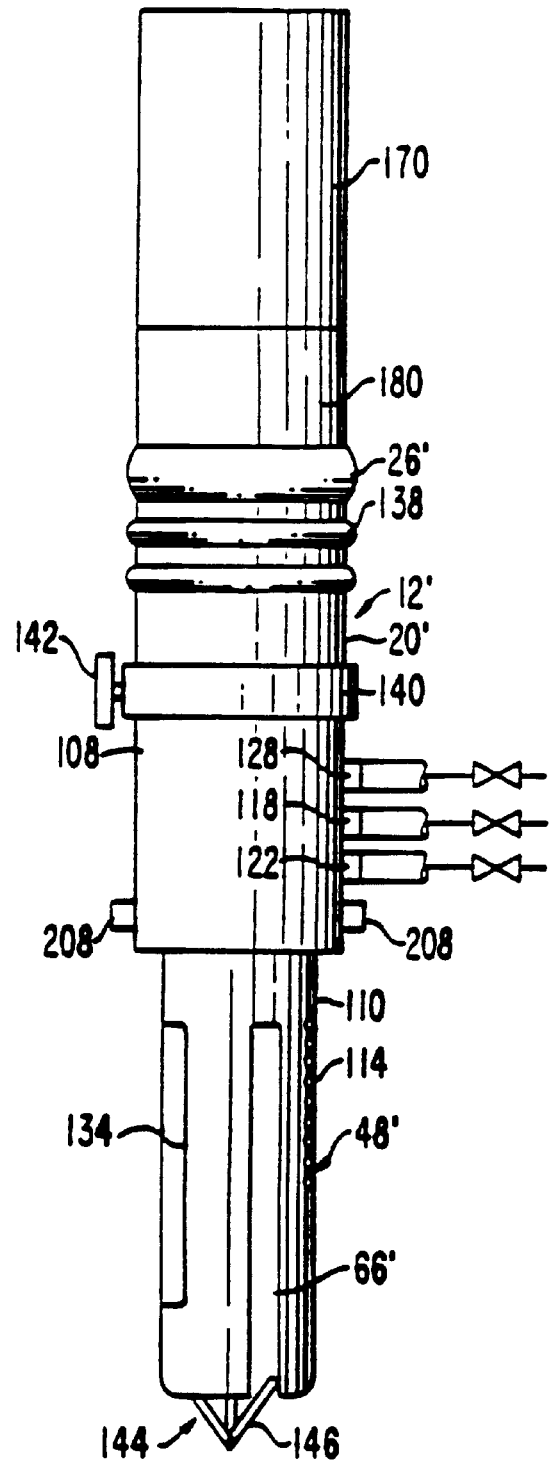

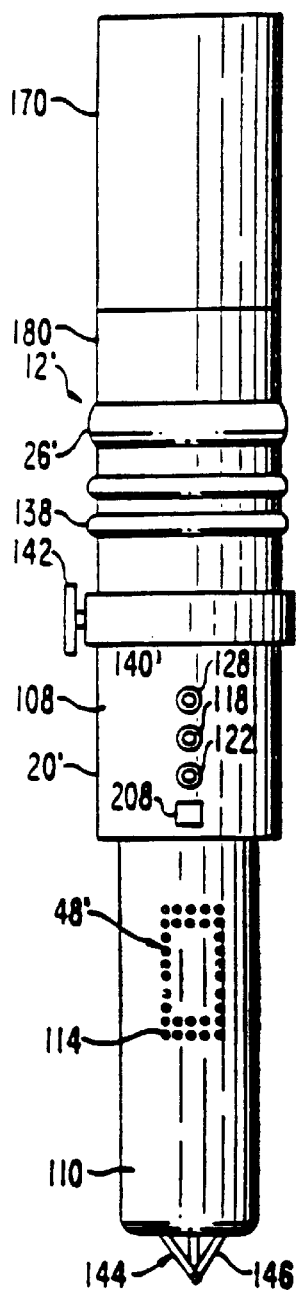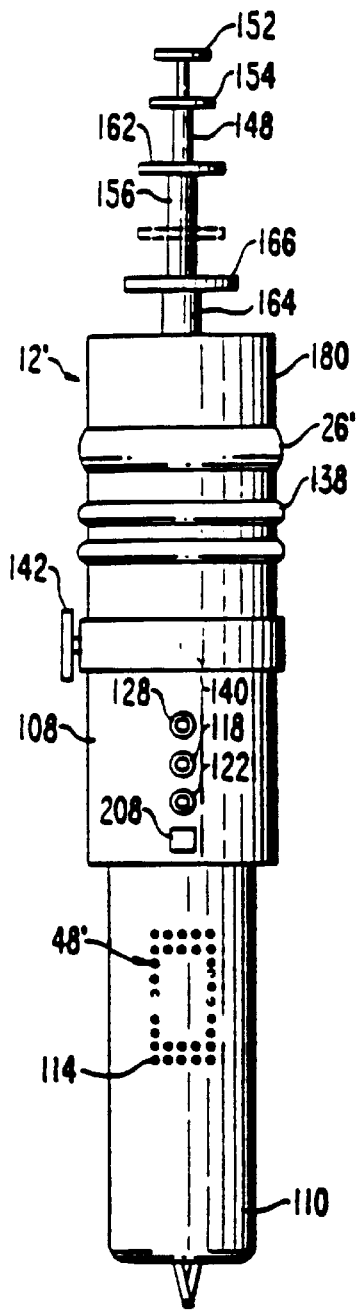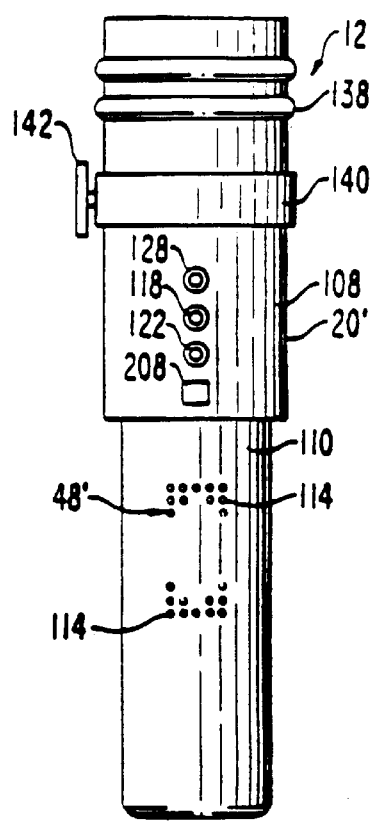

BLOOD VESSEL OCCLUSION DEVICE

This application is a continuation of application Ser. No. 08/714,887, filed Sep. 17, 1996, entitled BLOOD VESSEL TROCAR HAVING SIZE AND SHAPE VARYING INSERTION BODY, which is a continuation-in-part of U.S. patent application Ser. No. 08/479,408, filed Jun. 7, 1995, now U.S. Pat. No. 5,556,412, which is a divisional of U.S. patent application Ser. No. 08/209,280, filed Mar. 14, 1994, now issued as U.S. Pat. No. 5,499,996, which is a divisional of U.S. Pat. No. 07/808,767, filed Dec. 17, 1991, now issued as U.S. Pat. No. 5,330,498.

BACKGROUND OF THE INVENTION

1. Field of the Invention

This invention relates to cardiovascular surgical apparatus. More particularly, the invention relates to apparatus, a principle function of which is to more safely occlude the ascending aorta during the performance of surgery, such as open-heart surgery or minimally invasive cardiac surgery. Specifically, the invention relates to apparatus which may change size or shape, or both, during such use.

2. Description of Related Art

In many surgical procedures it is necessary to occlude a blood vessel in order to provide the surgeon with a bloodless field in which to work. Such occlusion is most commonly effected by the application of a vascular clamp to the concerned region of the blood vessel. In the performance of most open heart surgical procedures where occlusion of the ascending aorta is essential, however, the use of a vascular clamp for clamping this vessel creates a condition susceptible to serious negative consequences that the surgeon cannot completely control. For example, while the use of a vascular clamp to occlude the aorta provides a quick and easy occlusion of the vessel, clamping the aorta can disrupt the aortic wall, thereby dislodging degenerative plaque-like material, which is capable of migrating to the brain thereby resulting in a stroke. Other consequences can also result from clamping the aorta. For example, the dislodged particles may migrate to other parts of the body thereby creating the danger of limb gangrene in the extremities, such as the arms or legs, or damage to certain organs as, for example, the kidney, the liver or the small or large bowel. Alternatively, in clamping the aorta, the wall may rupture thereby resulting in hemorrhage. Each of these complications can cause serious morbidity and often times may result in death.

It is to the amelioration of these problems, therefore, to which the present invention is directed.

SUMMARY OF THE INVENTION

In accordance with a principle aspect of the present invention there is provided an occluder apparatus for obstructing the flow of blood in a blood vessel comprising an elongated hollow tubular body having a leading end sized for reception in said blood vessel, means for inserting said body through the wall of said blood vessel to extend said leading end into the interior of said blood vessel, an inflatable diaphragm carried in a collapsed, deflated condition within the interior of said body, means for conducting an inflating fluid from an external source into fluid communication with the interior of said diaphragm to effect expansion thereof, means in said body to enable release of said diaphragm in an inflated state from said body into flexible occluding engagement with the interior wall of said blood vessel about substantially the full circumference of a section thereof.

The invention contemplates use with the described occluder device of an external belt-like blood vessel wall-compressing device adapted to surround the blood vessel and apply a compressive force in opposed relation to the force applied by the occluder diaphragm. By use of the belt-like compressing device the blood vessel can be effectively occluded by the diaphragm without distention or distortion of the wall thereof thus to prevent flexure of the wall and dislodgement therefrom of fragile material that could create a dangerous condition in the patient.

Apparatus according to the invention can be particularly designed to facilitate several procedures common to open-heart surgery. For example, besides obstructing the flow of blood to the heart to create a quiescent region within which the surgeon can work, the apparatus can be designed to be useful in the introduction of myocardial preservation solution to the proximal region of the aorta. On the other hand, the passage designed to conduct myocardial solution can, alternatively, be connected to a pressure measuring device for monitoring aortic root pressure. Similarly, the passage can be employed for venting the aortic root and/or clearing the heart and aortic root of blood and/or air. Importantly, the apparatus can also be made to perform as an aortic arterial perfusion cannula for circulating blood between a heart-lung machine and the patient in bypass relation to the occluded region of the aorta and the heart.

To accomplish the purpose and function of the intravascular occluding device a compromise is made between the shape and size required to introduce the device and the shape and size of the device to perform its functions once it is intraluminal in a vessel. A device capable of altering its size or shape, or both, once it is placed intravascularly may satisfy both the size and shape requirements for insertion as well as the shape and size requirements for the medical function of the device once it is positioned in a vessel. The device may have the ability to alter its size and shape, or both, by fabricating a portion or portions of the device from materials soluble in a medium, such as a medium comprising blood. The portion or portions of the device may dissolve once it is positioned intravascularly, and that portion or those portions come in contact with the medium. The portion or portions of the device, which are fabricated from materials that are not soluble in the medium, are of a size or shape, or both, permitting the device to perform the desired medical function once it is intravascular. The solubility of the portion or portions of the device is dependent on (1) the material or the combination of materials, from which the device was fabricated, and (2) the type and characteristics of the medium to which the soluble portion or portions of the device is (are) exposed.

The soluble material may be organic, e.g. sugars, or inorganic, e.g., salts. Suitable soluble organic material may be selected from the group consisting of carbohydrates, such as glucose, sucrose, and mannitol; proteins; gelatins; plastics; lipids and lipid compounds; and polyethyl glycol, and combinations thereof. Similarly, soluble inorganic material may be selected from the group consisting of sodium chloride and sodium bicarbonate and the like Moreover, the soluble portion or portions may include a plurality of layers of soluble material, each of the plurality of layers having solubility characteristics different from at least another of the plurality of layers. Alternatively, the soluble portion or portions may include a honeycomb structural material and a honeycomb filling material, such that the honeycomb structural material and the honeycomb filling material have different solubility characteristics. For example, with respect to a particular medium, a portion or portions of a trocar body may include a non-soluble or soluble honeycomb structural material and a comparatively more soluble honeycomb filling material.

The medium may comprise a water-based medium, such as blood. Such blood may have hematocrit in a range of about 5 to 65%; hemoglobin in a range of about 2 to 18 grams; white blood cells in a range of about 1,000 to 50,000/cm$^2$; and platelets in a range of about 10,000 to 500,000/cm$^2$ Further, the blood may be saturated with oxygen in a range of about 5 to 100%, may include a partial pressure of carbon dioxide in a range of about 20 to 100 mm Hg, and may have plasma proteins in a range of less than about 8%, e.g., about 6 to 8%, by weight. It may also include inorganic substances in a range of about 0:1 to 2% by weight and may have a pH in the ranges of about 6.5 to 7.9. In another embodiment, the blood may be in various degrees of hemodilution with such substances as dextrose and water, saline, Ringer's Lactate, or plasma expanders. The blood also may have various pharmacological substances dissolved in it as may be given to a patient during medical treatment or in preparation for surgery, or both. The temperature of the medium may be in a range of about 1° to 41° C., but generally, the soluble portion or portions will dissolve more rapidly as the temperature of the medium increases.

In an embodiment, an occluder apparatus for obstructing the flow of blood in a blood vessel may comprise an elongated hollow tubular body having a leading end sized for reception in said blood vessel and including at least a portion of the body fabricated from a soluble material in order to alter the body's size or shape, or both, and means for inserting the body through the wall of the blood vessel to extend the leading end into the interior of the blood vessel. An inflatable diaphragm is carried by the body in a collapsed, deflated condition, and the apparatus includes means for conducting an inflating fluid from an external source into fluid communication with the interior of the diaphragm to effect expansion thereof The dissolving of the soluble portion or portions of the body may result in the release of the inflatable diaphragm. Alternatively, the apparatus may include means in the body to enable release of the diaphragm in an inflated state from the body into flexible occluding engagement with the interior wall of the blood vessel about substantially the full circumference of a transverse section thereof In another embodiment, an occluder apparatus for obstructing the flow of blood in a blood vessel comprises, in combination, an elongated hollow tubular body having a leading end for reception in the blood vessel and including at least one portion of the body fabricated from a soluble material in order to alter the body's size or shape, or both, and means for inserting the body through the wall of the blood vessel to extend the leading end into the interior of the blood vessel. Further, an inflatable diaphragm is carried by the body in a collapsed, deflated condition for insertion into the interior of the blood vessel, as well as, means for inflating the diaphragm to expand it about its periphery into cushioned occluding engagement with the interior wall of the blood vessel. The occluder apparatus also combines a belt-like pressurizing device including an inflatable cuff arranged to substantially surround the exterior of the blood vessel and to be expanded under the influence of fluid pressure into engagement with the exterior wall thereof in substantially opposing relation to the engagement of the interior wall of the blood vessel by the diaphragm and means for inflating the cuff.

It is, accordingly, an object of the invention to provide an improved apparatus for occluding blood flow in blood vessels in selected body sites, particularly in the ascending aorta, to facilitate surgical procedures.

It is another object of the invention to provide an effective blood vessel occluder in which the danger of dislodging brittle material from the wall of the blood vessel and the concomitant danger of creating serious morbidity is minimized.

Yet another object of the invention is to provide apparatus that permits the performance of multiple surgical functions and procedures through a single incision made in the blood vessel thereby eliminating the need to make plural incisions in the blood vessel commensurate with the number of procedures to be performed.

It is still another object of the invention to provide an apparatus including a soluble portion or portions that permit the size or shape, or both, of the apparatus to be varied in order to facilitate insertion or removal of apparatus from a patient's body.

For a better understanding of the invention, its operating advantages, and the specific objectives obtained by its use, reference is made to the accompanying drawings and description which relate to preferred embodiments of the invention.

BRIEF DESCRIPTION OF THE DRAWINGS

FIG. 3 is a perspective representation of the occluder apparatus according to the invention in an intermediate stage of installation;

FIG. 10 is a view of the diaphragm mounting plate with the diaphragm removed;

FIG. 11 is a view illustrating the diaphragm in an inflated condition;

FIG. 17 is a sectional elevational view of a trocar body as shown in FIG. 14 carrying an occluder diaphragm in its deflated condition;

FIG. 18 is a sectional view taken along lines 18—18 of FIG. 17;

FIG. 19 is an elevational view of the trocar of FIG. 14 as viewed from the distal side;

FIG. 20 is an elevational view of the trocar as viewed from a lateral side;

FIG. 21 is an elevational view of the trocar as viewed from the proximal side;

FIGS. 22 and 23 are views similar to FIG. 21 illustrating the trocar of FIG. 14 in various stages of installation;

DETAILED DESCRIPTION OF THE PREFERRED EMBODIMENTS

Figure 1:
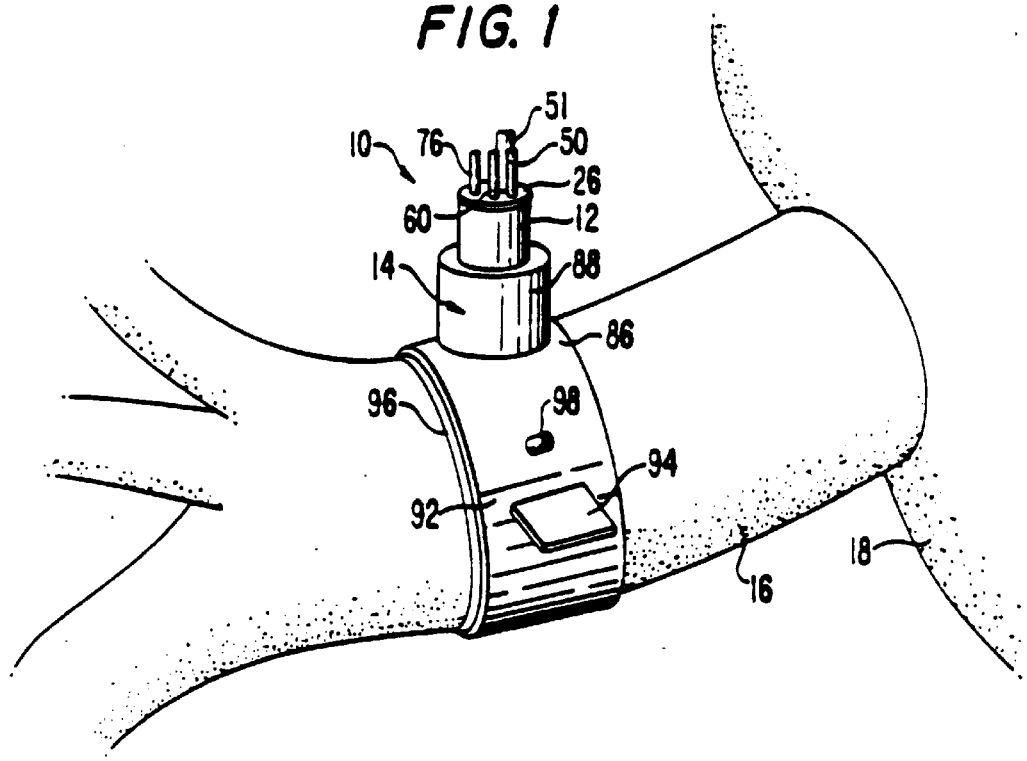
FIG. 1 is a perspective representation, partly schematic, of an occluder apparatus operatively associated with a pressurizing belt according to the invention.
Figure 8:
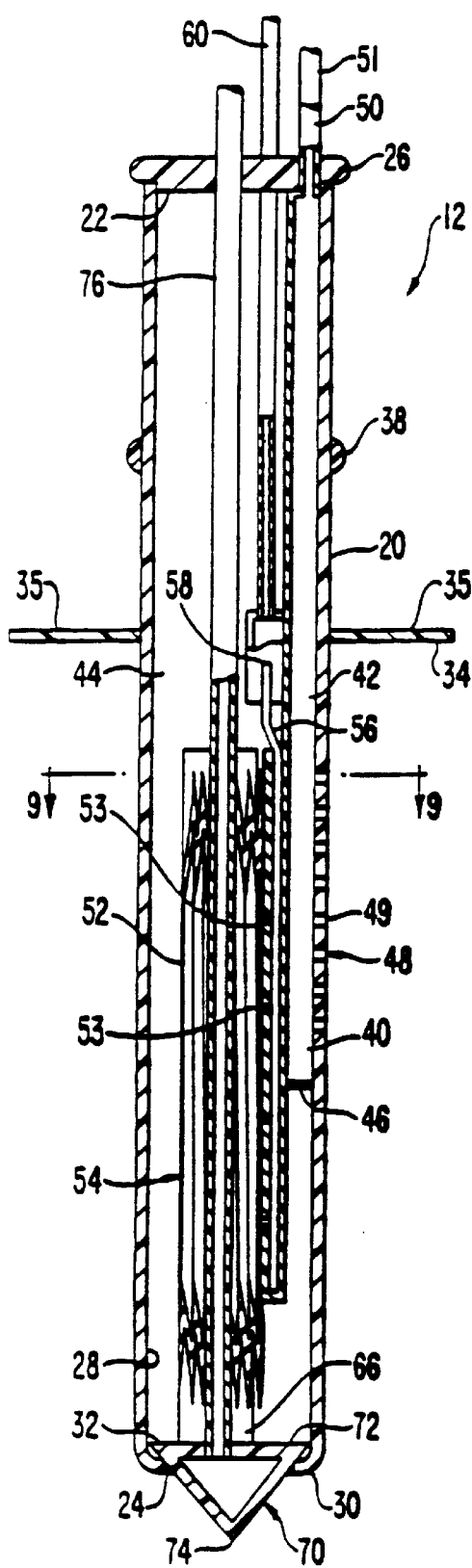
FIG. 8 is a sectional elevational view of a trocar body carrying an occluding diaphragm in its deflated condition.

Referring particularly to FIG. 1 there is shown a blood vessel occluder apparatus, indicated generally at 10, comprising an elongated tubular trocar 12 which is held in its operative position by pressurizing belt 14 in a blood vessel 16, here shown as the ascending aorta connecting with the heart muscle 18. The details of construction of the trocar 12 are best shown in FIG. 8 as comprising an elongated, hollow, generally cylindrical tubular shell 20 formed of a relatively hard plastic material, such as a polycarbonate material, that is open at both its upper and lower ends, 22 and 24 respectively. The opening at the upper end 22 of the shell 20 is closed by a closure cap 26 having openings therein to permit passage of fluid-conducting members, as hereinafter described. The opening at the lower end 24 of shell 20 is of slightly smaller diameter than that of the internal wall surface 28 of the shell, being defined by an in turned flange 30 forming a substantially annular shoulder 32 about the opening.

An annular flange 34 extends radially outwardly from the exterior surface of the shell 20 at an intermediate location along the length thereof. The flange 34 is adapted to receive sutures 36 (FIG. 3) for fixedly attaching the trocar 12 in position on the wall of the blood vessel.

Locking detects 38 formed of slightly compressible material are bonded to the shell surface and project radially outwardly from opposite sides thereof at a level about midway between the flange 34 and the upper end 22 of the shell. In the preferred embodiment of the invention, these detects 38 cooperate with locking means in the pressurizing belt 14, as hereinafter described, for establishing the positional relationship between the trocar 12 and the belt 14 prior to operation of the occluder apparatus 10 according to the invention.

Figure 9:
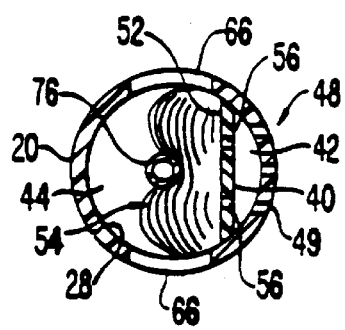
FIG. 9 is a cross-sectional view taken along line 9—9 of FIG. 8.

As shown in FIGS. 8 and 9 the interior of the tubular shell 20 forming the trocar 12 is divided longitudinally by a partition plate 40 into transversely spaced regions indicated by the numerals 42 and 44, respectively. The plate 40, as shown best in FIG. 9, extends chordally across, the interior of shell 20 and has its opposite side edges sealedly attached to internal wall surface 28. The lower end of partition plate 40 is spaced upwardly from the lower end 24 of the shell 20 and attaches a closure plate 46 to define region 42 as a fluid conducting passage. A flow opening 48, which may be an enlarged solitary opening in the wall of shell 20 or, as shown, formed of a plurality of small diameter openings 49 extending therethrough, effects fluid communication between the passage 42 and the exterior of the trocar 12. A line 50 extends through the closure cap 26 and fluidly connects the other end of the passage 42 to a fluid source, as for example a source of myocardial preservation solution, on the exterior of the trocar.

In the described apparatus, the passage 42 can, during alternate periods of operation, be employed to establish fluid communication between the interior of the blood vessel 16 and a pressure monitor (not shown) via the opening 48 and a flow line 51 that, at one end, extends through the cap 26 to communicate with the passage 42 and, at the other end, connects with the pressure monitor.

A second chordally extending plate 52 extends across the interior of the shell 20 parallel to, but slightly spaced from, the plate 40. The plate 52 contains a plurality of small diameter through-openings 53, typical examples of which are shown in FIGS. 10 and 11, and on its surface facing the interior region 44 of the trocar body 12 mounts an expandable occluder diaphragm 54 formed of thin walled, flexible material, such as polyeurathane. The space between plates 40 and 52 contains a pair of conductors 56 extending downwardly from a manifold 58 that mounts a fluid-conducting tube 60 for conducting saline activating fluid to the interior of the diaphragm 54 for inflating and expanding it into its operative condition. Flow distribution between the openings 53 in partition plate 52 and respective regions of the diaphragm 54 is effected by small diameter passages 55 that extend between the openings 53 and similar openings 57 in the diaphragm wall.

Figure 6:
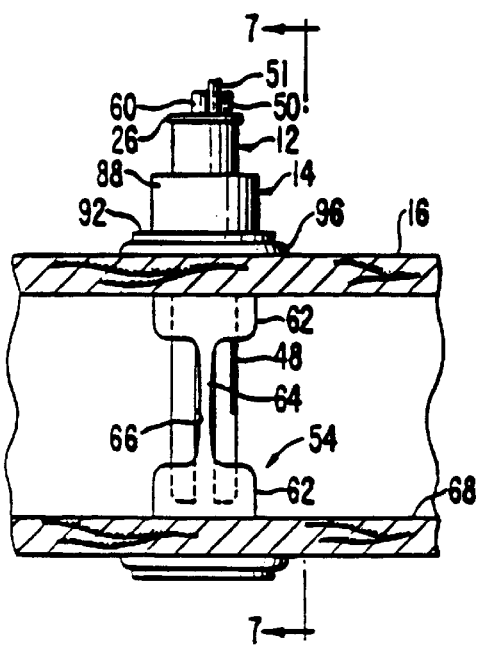
Figure 7:
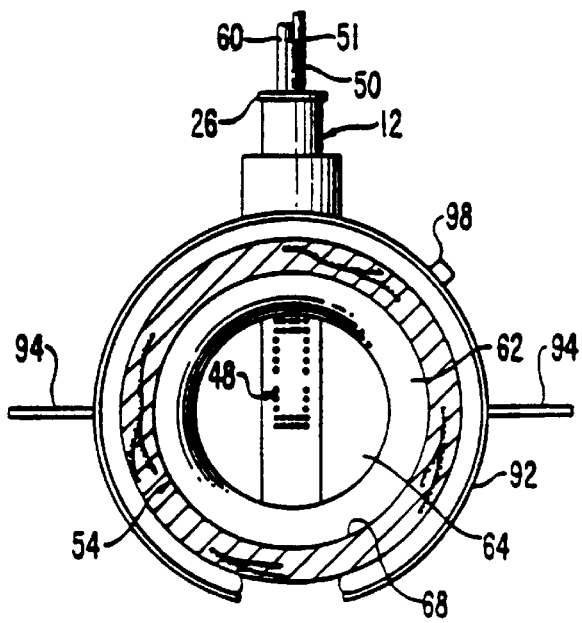
FIG. 7 is a sectional view of the occluder apparatus and pressurizing belt taken along line 7—7 of FIG. 6.

In its expanded condition the diaphragm 54 assumes a shape corresponding essentially to that illustrated in FIGS. 6, 7, and 11 comprising a generally toroidally-shaped cushion portion 62 and a membrane portion 64 that fills the region of the diaphragm interiorly of the cushion portion. Upon inflation with saline fluid the diaphragm 54 is permitted to expand exteriorly of the trocar 12 by means of a pair of aligned, oppositely spaced slots 66 that extend upwardly from the open lower end of the shell 20. The slots 66 are so positioned in the shell 20 with respect to the diaphragm 54 in its deflated condition to enable it to readily project laterally outwardly into engagement with the interior wall 68 of the blood vessel 16. Thus, when expanded, the diaphragm 54 effectively occludes flow through the blood vessel 16 with the opening 48 in shell 20 being disposed in facing relation to the proximal side of the apparatus.

The apparatus 10 contains an expandable penetrating plug 70 that, when expanded, is conical in shape. The base 72 of plug 70 has a peripheral diameter permitting its engagement with the shoulder 32 formed at the lower end of shell 20. The apex 74 of the plug 70 extends axially outwardly from the open lower end 24 of the trocar body 12 to form a pointed tip suitable for penetrating the wall of the blood vessel 16 to permit insertion therein of the lower portion of the trocar after an incision has been made in the blood vessel wall.

The plug 70 is hollow and has walls formed of an expandable flexible material, such as polyeurathane. A substantially rigid, elongated tube 76 attaches at its lower end to the base 72 of the plug 70 with the passage through the tube in fluid communication with the hollow interior of the plug. The upper end of the tube 76 extends through a self-sealing opening in the cap 26 to connect with an exterior source of saline fluid.

Figure 2:
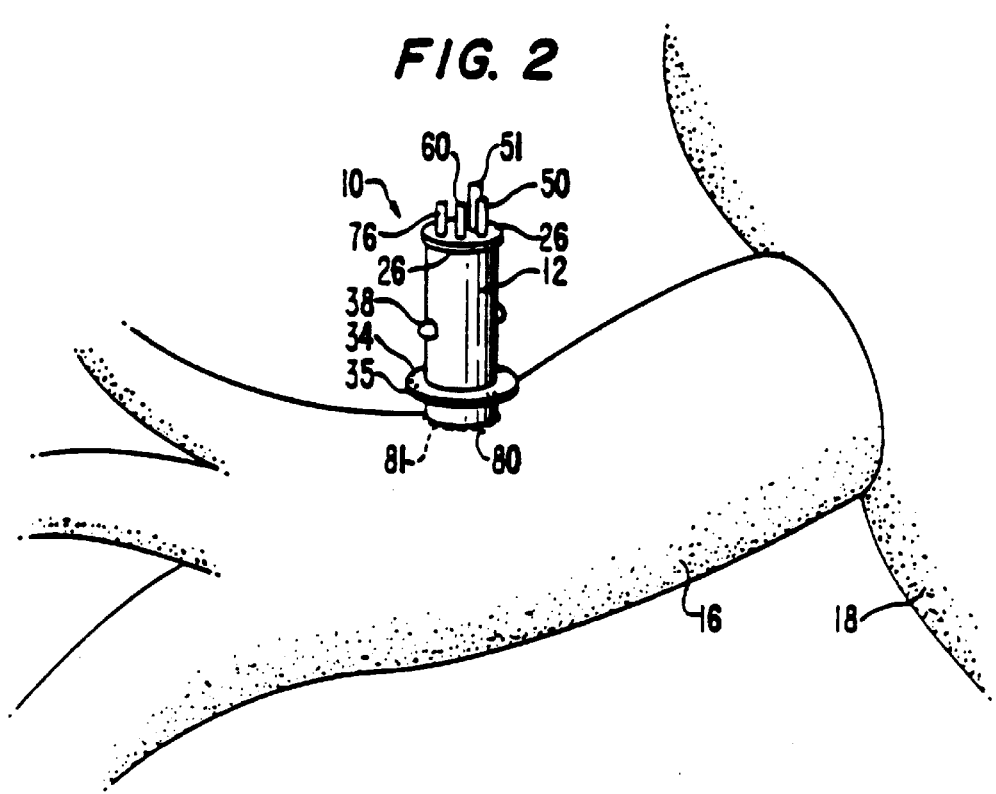
FIG. 2 is a perspective representation of the occluder apparatus according to the invention in a preliminary stage of installation.
Figure 4:
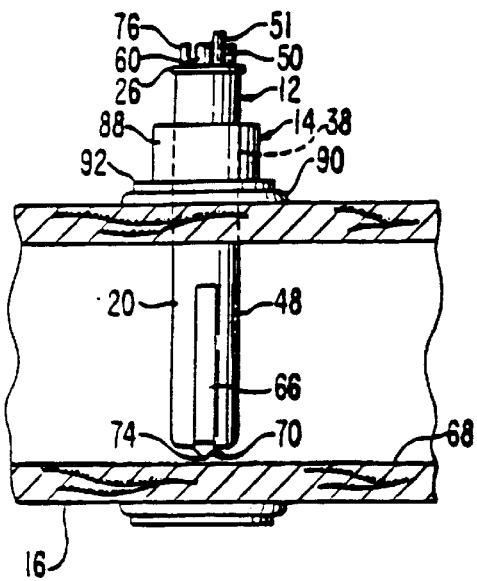
FIGS. 4 through 6 illustrate an embodiment of the invention in various operative stages when installed in a blood vessel.
Figure 5:
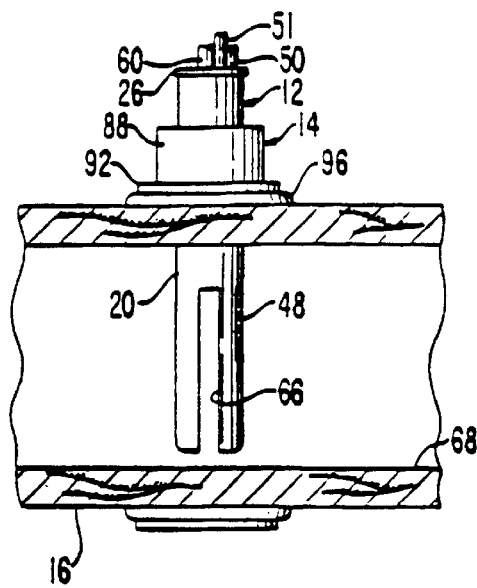

In practice, the trocar 12 is inserted radially through the wall of the blood vessel 16 by the surgeon's first making an incision 80 (FIG. 2) therein of an extent sufficient to permit insertion of the shell 20. The incision will be of such extent as to create an opening in the blood vessel wall of such an extent as to cause the shell 20 to be snugly received therein. (In preparation for closing the opening formed by the incisions 80, the surgeon may install a purse-string suture 81 about the opening). Thereafter, assisted by the piercing tip formed by the expanded plug 70, the trocar is caused to penetrate the blood vessel under the impetus of a downwardly-directed manual force applied to the trocar 12. The extent of insertion of the trocar into the interior of the blood vessel 16 is limited by the flange 34 which, when placed in engagement with the exterior surface of the wall of the blood vessel, will locate the tip 74 of the plug at, or closely spaced from, the blood vessel wall opposite the incision 80.

Next, by properly aligning the trocar with the longitudinal axis of the blood vessel 16, as by means of guide marks (not shown) on the surface of the flange 34, proper disposition of the trocar can be determined such that the elongated slots 66 are aligned transversely across the blood vessel section. Sutures 36 are then applied via openings 35 formed in the flange 34 to securely attach the flange to the wall of the blood vessel 16.

Following this step, the fluid employed to expand the plug 70 is released therefrom by venting the fluid through the tube 76. Upon collapse of the plug walls, the tube 76 is withdrawn through a self-sealing opening in the cap 26 that accommodates passage of the collapsed plug.

With the trocar 12 thus installed in the blood vessel 16 the more basic functions contemplated for the occluder apparatus 10 can be achieved. For example, when inflating fluid, such as saline liquid, is admitted at pressures controlled by a valve (not shown) provided in the line 60, the fluid flows into manifold 58 and through the conductors 56 and the openings 53 in the partition plate 52 into the collapsed diaphragm 54, inflation will occur whereby the diaphragm will be caused to expand, with expansion beyond the confines of the shell 20 being permitted by means of the laterally facing openings therein created by the elongated slots 66. In expanding, the outer peripheral edge of the toroidally-shaped cushion portion 62 of the diaphragm 54 is, as best shown in FIGS. 6 and 7, caused to engage the inner wall surface 68 of the blood vessel 16 about substantially the entire circumference thereof. The material of which the diaphragm is constructed being of thin, light weight construction, and the pressure of the inflating fluid being appropriately controlled, the cushion portion 62 of the diaphragm is caused to closely envelop the shell body while conforming to the blood vessel wall tissue surface configuration so that an effective blood flow-occluding obstruction is effected in the blood vessel 16 without significant distention or description of the blood vessel wall.

Where the described apparatus 10 is employed for aortic occlusion, with the patient effectively connected to a heart-lung machine in a manner well known in the surgical arts, it will be appreciated that, as well as providing the surgeon with a quiet, bloodless field on the proximal side of the occlusion within which to operate, the apparatus permits the practice of other procedures, as well. For example, with line 50 connected to a source of myocardial preservation solution or blood cardioplegia, by periodic operation of a control valve (not shown) this solution can be supplied intermittently through passage 42 and exiting the trocar through the holes 49 forming opening 48 to the root of the aorta for perfusion through the coronary arteries into the heart muscle 18 to preserve and arrest the heart, thereby to facilitate the performance of a surgical procedure.

Also, during periods in which the line 50 is not employed for the supply of myocardial preservation fluid, it can be conveniently employed, by means of a suitable bypass connection containing valving to an evacuation pump (not shown), for removing blood from the heart via the aorta root thereby preventing the accumulation of blood in the heart and maintaining the heart in a collapsed condition whereby the practice of a surgical procedure on the heart can be facilitated.

Furthermore, the bypass connection attached by way of line 50 to apparatus 10 can also be employed, during the occlusion period or following completion of the surgical procedure on the heart and deflation of the occluder, for the evacuation of any air bubbles from the heart chambers and the ascending aorta.

Still further, with the opening 48 in the trocar shell wall 20 positioned closely adjacent the wall surface 68 in the upper region of the aorta passage, the line 50 can be effectively employed as a vent for removing air bubbles in the blood as it is pumped into the ascending aorta from the heart upon collapse of the occluder diaphragm 54 when expansion fluid is released from the line 60 and the heart resumes its contraction. Use of the occluder apparatus 10 for this purpose is most advantageous because the protrusion of the trocar into the aorta will create turbulence in the blood flow and the presence of the collapsed diaphragm 54 in the blood flow passage will tend to partially obstruct and retard the blood flow in this region and the entrained air bubbles will migrate upwardly whereby there evacuation through the opening 48 is enhanced.

Figure 12:
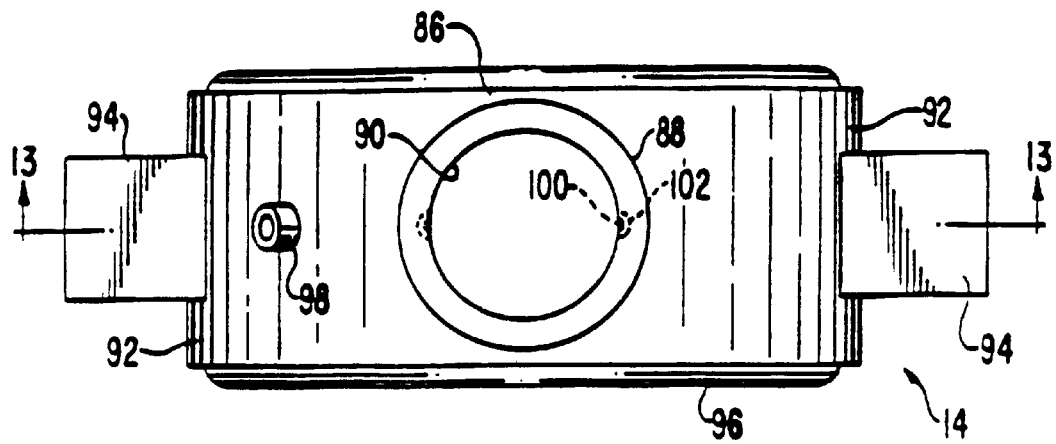
FIG. 12 is a plan view of a pressurizing belt according to the invention.
Figure 13:
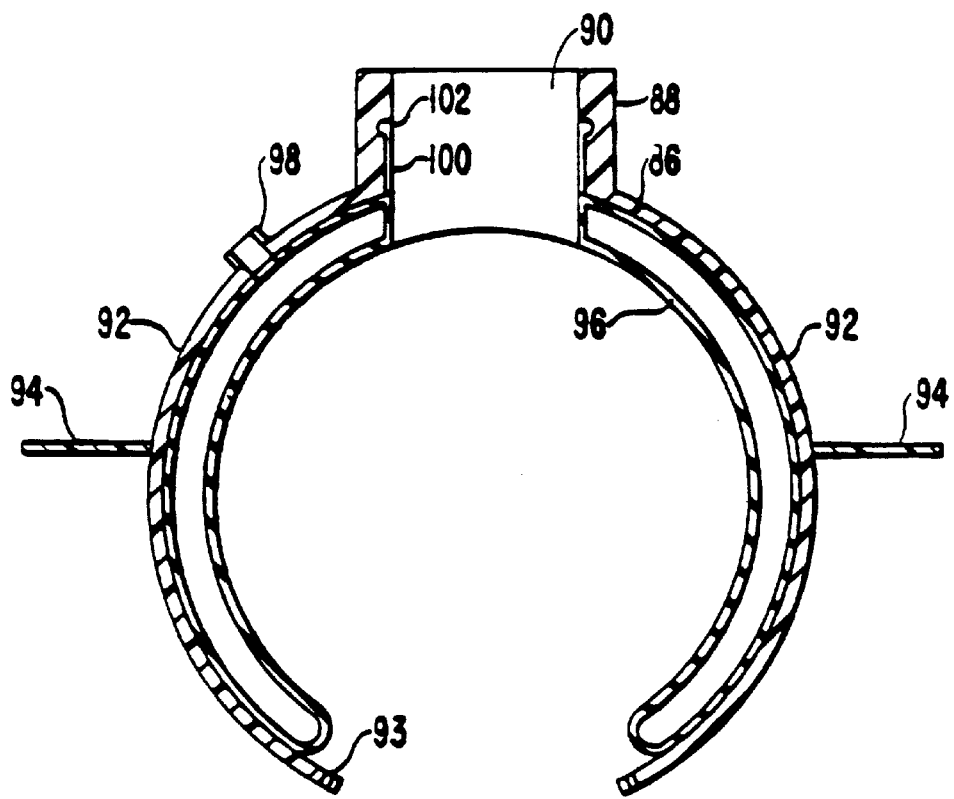
FIG. 13 is a sectional view taken along line 13—13 of FIG. 12.

Notwithstanding the capability of utility of the apparatus 10 in the above described manner, in its preferred mode of operation, the apparatus will be used in association with a pressurizing belt 14, the details of construction of the embodiment of FIG. 1 of which are best illustrated in FIGS. 12 and 13 herein. Accordingly, the belt 14 comprises a base 86 containing an upstanding collar 88 having a through-opening 90 that permits passage of the trocar 12. The base 86 is generally C-shaped and defines wings 92 on opposite sides of the collar 88 to form a strap-like structure. Openings 93 adjacent the terminal ends of the wings 92 are adapted to receive sutures for securing the wings to the blood vessel. The base 86 is formed of a plastic material, such as a polycarbonate material, having sufficient rigidity to impart strength to the construction, yet being sufficiently flexible to permit the wings 92 to flex, thereby enabling them to enclose the blood vessel 16 without distortion thereof upon manual manipulation of operating tabs 94 that are integrally formed on or bonded to the respective wings. The undersurface of the base 86 which, in operation, faces the exterior of the blood vessel 16 has attached thereto by means of bonding, or the like, an inflatable cuff 96 formed of soft, pliable material. An inflating fluid inlet 98 is formed on one of the wings 92 and contains a passage that communicates with the interior of the cuff 96 whereby an inflating fluid can be supplied or released in order to expand or retract the cuff into and out of compressing relation with the enclosed blood vessel 16.

As shown, the opening 90 in collar 88 is formed along its wall with opposed channels 100, at the top of both of which is formed a cup-shaped recess 102. These structural elements cooperate with the detects 38 on the external surface of the trocar shell 20 to positionally fix the trocar 12 with respect to the belt 14 and thereby establish the transverse disposition of the slots 66 in the shell with respect to the blood vessel section.

In the described embodiment of the invention, after the trocar 12 is sutured to the blood vessel 16, the pressurizing belt 14 is mounted thereon with the collar 88 telescopically received on the upper portion of the trocar shell 20 that projects from the blood vessel wall. As the collar 88 is slid into position the opposed detects 38, which are of compressible material, slidingly engage the channels 100 where they are compressed. Upon reaching the cup-shaped recesses 102 the detects 38 expand into the recesses to lockingly set the positional relationship between the trocar 12, the pressurizing belt 14 and the blood vessel 16.

Importantly, as best shown in FIG. 6, upon completion of the assembly of the pressurizing belt 14 and the trocar 12, the cuff 96 on the belt is disposed on the opposite side of the wall of blood vessel 16 from the occluder cushion 62. In the preferred practice of the invention, the line 60 that supplies saline liquid for expanding the diaphragm 54 is connected in parallel with the inlet 98 to the cuff 96 on the pressurizing belt 14. Thus, the expansion fluid is admitted simultaneously to both the occluder diaphragm 54 and to the cuff 96 so that occlusion of the blood vessel flow passage is accomplished without danger of either compression or distention of the wall thereof Moreover, because the material that forms both the cushion 62 of the diaphragm 54 and the cuff 96 on the belt 14 is soft and pliable and thereby readily conformable to the blood vessel wall structure, it will be appreciated that upon expansion of these members occlusion is accomplished without danger of dislodging fragile material or brittle tissue from the wall of the blood vessel or of squeezing atherosclerotic material into the vessel passage.

Figure 24:
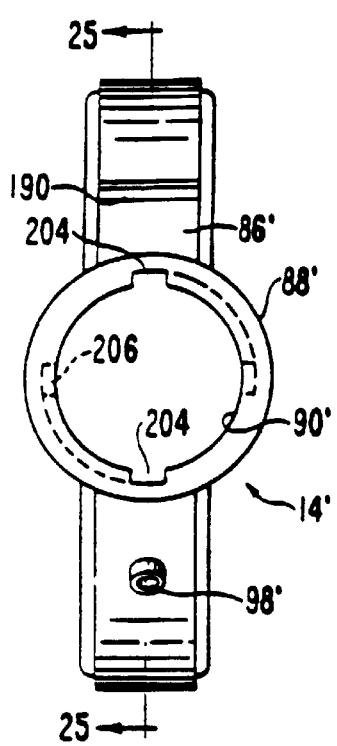
FIG. 24 is a plan view of an alternate form of pressurizing belt according to the invention.
Figure 26:
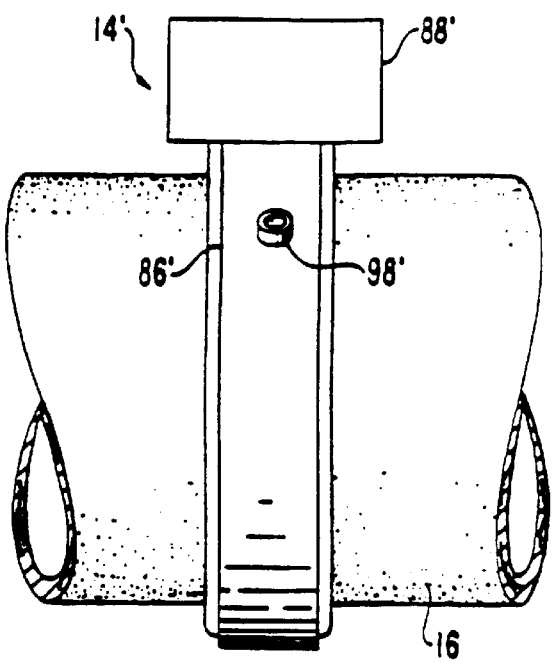
FIG. 26 is an elevational view of the pressurizing belt of FIG. 12 in operative position on a blood vessel.
Figure 25:
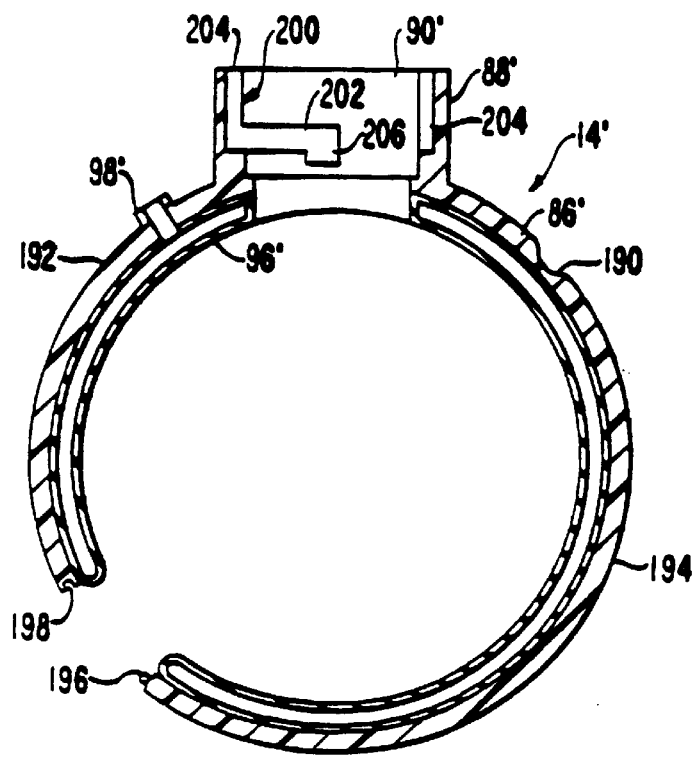
FIG. 25 is a sectional view taken along line 25—25 of FIG. 24.

FIGS. 14 to 23 illustrate another trocar organization 12, which is constructed according to the invention and FIGS. 24 to 26 illustrate an alternate form of pressurizing belt 14' employing a collar 88' which is particularly adapted for use with the trocar organization of FIGS. 12 to 23 but whose base portion 86, can be used interchangeably with that of the belt 14.

Figure 14:
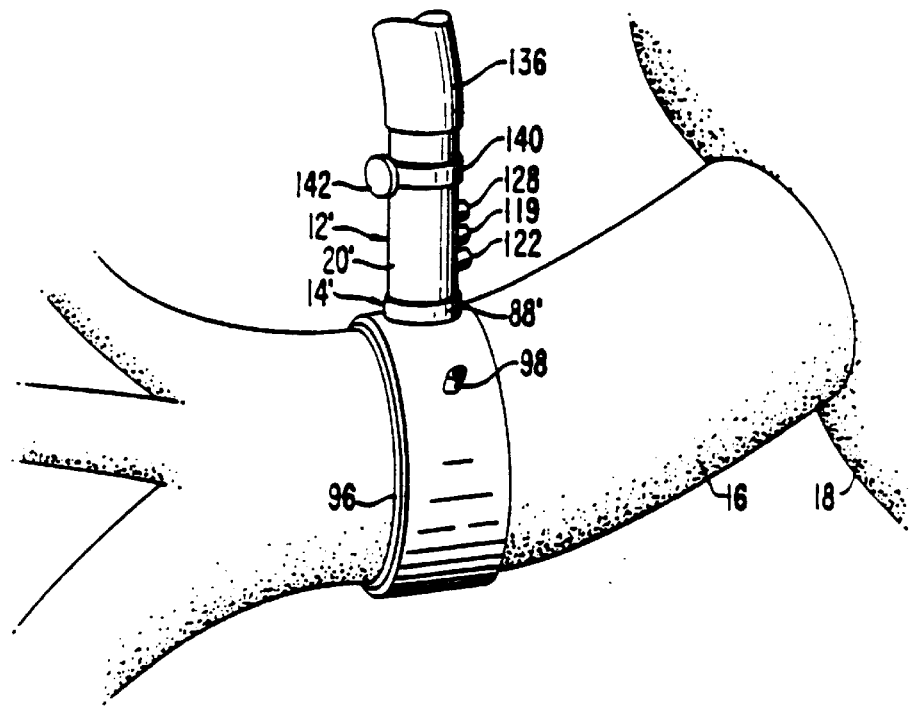
FIG. 14 is a view, similar to FIG. 1, illustrating another embodiment of the occluder apparatus and pressurizing belt according to the present invention.
Figure 16:
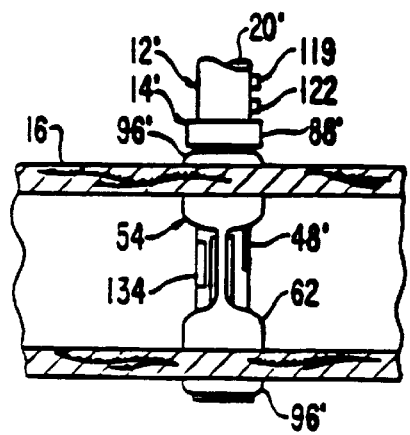
FIG. 16 is a partial sectional view taken perpendicularly of FIG. 15.
Figure 15:
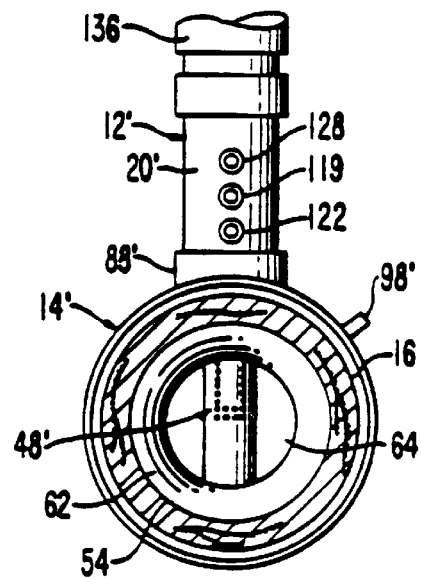
FIG. 15 is a sectional view illustrating the occluder apparatus of FIG. 14 in operative position within a blood vessel.

With reference to FIG. 14, which is a view similar to FIG. 1, there is illustrated a modified form of trocar 12' operably assembled with the modified form of pressurizing belt 14' and applied to an ascending aorta 16 connected with heart muscle 18. In the practice of this form of the invention, the pressurizing belt 14' is first applied to the walls of the blood vessel 16 and thereafter the trocar 12', equipped with scalpel blades 146 (FIG. 17), as hereinafter described, incises the wall of the blood vessel 16 as the trocar is extended into the belt collar 88'. The construction of the trocar 12', moreover, is such as to permit, besides the functions described for the embodiment of FIGS. 1 to 11, the additional functions of operation of an aortic arterial perfusion cannula for circulation of blood between the patient and a heart-lung machine, with all such functions being achieved form a single incision made in the aorta wall upon application of the trocar into the collar 88' of the pressurizing belt 14'.

Accordingly, as best shown in FIG. 17, the trocar 12' comprises a generally tubular shell 20', the wall of which is formed intermediate its upper and lower ends with an annular shoulder 106 that divides the shell into a larger diameter upper portion 108 and a reduced diameter lower portion 110. Shoulder 106 operates to limit the extent of penetration of the trocar into the aorta passage.

The upper end of the shell 20' is closed by a closure cap 26' having a single opening formed with self-sealing capability to permit passage of a blade assembly 144 along the shell axis and refractive withdrawal of the blade assembly at an appropriate point in the operational procedure of the apparatus, as hereinafter described. As shown, the trocar shell 20' is provided in the lower portion 110 with laterally aligned elongated slots 66' extending upwardly from the lower end of the shell to permit egress of the occluder diaphragm 54 upon application of the inflating fluid thereto.

The lower portion 110 of the shell 20' is provided on one side of the slots 66', with a discharge opening 48', here shown as a plurality of small diameter holes 49', for communicating an internal passage 42' formed by a chordally disposed plate 116 and a cover plate 118 with the proximal side of the trocar 12'. The passage 42' contains two sources of communication with the exterior. The first, comprising an inlet connection 119 in the shell wall and an abbreviated fluid line or elbow 120 that fluidly connects the connection 119 with the interior of the passage 42', serves to supply myocardial preservation solution to the aorta, in a manner as previously described, when the trocar is operably installed in the aorta. By means of a second fluid connection 122 communicating with the passage 42' the trocar can also be connected to a pressure monitor device (not shown) by means of which, and through appropriate manipulation of the respective valves 124 and 126 in the lines attaching with the connectors 119 and 122, the passage 42' can be utilized alternately as a means for supplying myocardial preservation solution and as a means for detecting the pressure in the aorta between the intervals during which the myocardial preservation solution is supplied and before or after the occluder is distended to measure the blood pressure in the ascending aorta.

As in the previous embodiment, the occluder diaphragm 54 is attached to a second chordally extending plate, here indicated as 52', that is spaced from the first plate 116. The diaphragm 54 communicates with a source of saline inflating liquid via inlet connection 128 that is connected to a manifold 58', via the internal conductor 130 with conductors 56' interconnecting the manifold with openings 53, formed in the plate 52'. Similar to the previously described apparatus, the inflating fluid supply line connecting with the manifold 58' is desirably made common with the inlet connector 98 to the belt cuff 96 in order that inflating fluid is delivered substantially simultaneously to both the diaphragm 54 and to the belt cuff in order to insure an equalization of the compression applied to the opposed surfaces of the blood vessel wall.

The interior region 132 of the trocar shell 20', exteriorly of the passages 42' and 56' formed by the partition plates 52 and 116, defines a passage included in the blood circulating line between the patient and a heart-lung machine (not shown). To render such circulating flow effective, the trocar shell 20' is provided in the lower portion 110 on the side of the slots 66' opposite that containing the opening 48', with an elongated opening 134 that is sufficiently sized to accommodate blood flow from the heart-lung machine and return to the ascending aorta on the distal side of the expanded occluder diaphragm 54, as hereinafter more fully described. Connection from the heart-lung machine to the end of the trocar upper portion 108 is made by means of a tubular feed line 136 (FIG. 14) that is fixedly attached to the shell by means of connecting elements 138 of well-known type on the exterior surface of the shell 20', which cooperate with complimentary elements in the line. A valve mechanism 140 operated by actuating knob 142 is effective to open and close the flow circulating line as further explained herein.

Extending axially of the shell 20' is the blade assembly, indicated generally by reference numeral 144. It includes a plurality of articulated scalpel blades 146, here shown as being three in number disposed on 120° angular spacing but which may comprise a greater or lesser number of blades. The blades 146 are arranged to be retractably extended from the opening 27' at the tip of the lower portion 110 of shell 20' whereby, when the trocar 12' is inserted by the surgeon longitudinally into the belt collar 88', the blades are effective to incise the wall of the aorta to permit penetration thereof by the lower portion I 10 of the trocar apparatus.

The blade assembly 144 comprises an axially disposed support rod 148, to the leading end of which each of the blades is attached by a pivot connection 150 thereby forming a sharp point. At its upper end the blade support rod 148 contains an operating head 152 and a spacer flange 154 axially spaced therefrom. Support rod 148 is concentrically received in an axially elongated support sheath 156 for relative sliding movements there-between. Articulating links 158 connect the rear ends of the respective blades 146 to the leading end of sheath 156 by means of pivot connections 160. An operating flange 162 at the rear end of the sheath 156 effects movement of the sheath with respect to the support rod 148 whereby extension of the sheath downwardly causes the respective blades 146 to be angularly displaced outwardly into engagement with the shoulder 32' formed by the in turned flange 30, that defines the opening 27' at the lower end of the shell 20'.

The sheath 156 is concentrically enclosed by an elongated carrier sleeve 164 having an operating flange 166 at its rear end. The leading end of the carrier sleeve 164 contains a plurality of circumferentially spaced containment slots 168 adapted to receive the respective articulated links 158 and blades 146 when the sheath 156 is retracted into the carrier sleeve prior to withdrawal of the blade assembly 144 from the trocar 12'.

In order to properly position the elements of the blade assembly 144 prior to inserting the trocar 12' into the belt collar 88' the apparatus includes an applicator cover 170, here shown as being a cylindrical shell having a closure plate 172 at the top and an interior integrated stepped sleeve 174 having lands 176 and 178 adapted to engage the operating flanges 162 and 166 on the rear ends of the sheath 156 and carrier sleeve 164, respectively. The undersurface of the closure plate 172, as shown, provides the bearing surface for the operating flange 152 on the support rod 148.

The lower end of the applicator cover 170 is arranged to seatedly engage the upper surface 182 of a hollow cylindrical spacer 180. As shown, the opposed upper and lower surfaces 182 and 184, respectively, of the spacer 180 contain aligned axial openings 186 and 188 to accommodate passage of the blade assembly 144. The lower surface 184 of the spacer 180 engages the facing surface of the closure cap 26' to create a substantially rigid structure extending the full length of the assembled trocar apparatus.

The pressurizing belt 14' adapted for use with this embodiment of the apparatus is particularly illustrated in FIGS. 24 to 26. It comprises a base structure 86' having an upstanding collar 88', the latter containing a through-opening 90', for reception and passage of the trocar 12'. The base structure 86' is adapted to completely surround the aortic blood vessel 14 and for this reason contains a hinge 190 on one side of the collar 88' that divides the base into two wings, one of which 192 contains the collar and inflating fluid connector 98' and the other 194 of which has a locking detent 196 formed at its end for engagement with a cooperating notch 198 in the end of wing 192. As in the previously-defined belt structure 14 the undersurface of the base 86' attaches an expandable cuff 96', the interior of which fluidly connects via connector 98, with a source of inflating fluid (not shown).

The collar 88' differs from that in the previous embodiment of pressurizing belt 14 in that the through-opening 90' is formed to accommodate downward reception of the trocar 12'. This opening 90' is also provided with a locking device, here shown as a bayonet-type connection 200, defined by opposed grooves 202 formed in the wall of the opening. Each groove 202 has an open upper end at 204 in the wall of the collar opening 90' and a seat 206 at the lower end thereof, whereby a pair of diametrically opposed projections 208 on the exterior surface of the upper portion 108 of trocar 12' are caused to traverse the grooves as the trocar is projected into the belt collar 88' causing the trocar to undergo approximately 90° rotation about its longitudinal axis for ultimate seating in the seats 206 to effectively lock the trocar 12' with respect to the belt collar.

As shown in FIGS. 19 through 23, the projections 208 are positioned diametrically on the external surface of the shell 20', with each being disposed in substantial alignment with the openings 48 and 134, respectively. Thus, with the projections 208 lockingly received in the respective bayonet seats 206, the slots 66' are positioned transversely of the blood vessel passage in order to render the diaphragm 54', when activated, effective to occlude flow through the passage.

The operation of this embodiment of the invention is as follows. Following incision of the chest cavity by the surgeon to expose the ascending aorta 16 and heart muscle 18 and selection of the position along the aorta at which occlusion of the blood vessel will be effected, the pressurizing belt 14' is mounted to the blood vessel 16 by first spreading the wings 192 and 194 by means of hinge 190 to permit reception of the belt around the blood vessel without distortion thereof and, thereafter, insertion of the detent 196 into the slot 198 to lock the belt in surrounding relation to the aorta.

Next, the trocar 12', with the valve 140 actuated to its open position and with the blade assembly 144, applicator cover 170 and spacer 180 in position is inserted into the opening 90' of the collar 88' of the pressurizing belt 14' by registering the projections 208 on the exterior of the trocar shell 20' with the open ends 204 of the slots 202 of the bayonet connection 200. As the projections 208 move along the vertical portions of the respective slots 202, the blades 146 incise the wall of the aorta whereby the trocar 12' is caused to penetrate into the interior of the aortic passage. The length of the lower portion 110 of the shell 20' is such that, when the shoulder 106 engages the aorta outer wall the tips of the blades 146 are slightly spaced from the aorta inner wall on the side opposite the incision. This spacing of the tips of blades 146 from the opposite side of the aorta wall is further controlled by the cooperation between the projections 208 and the bayonet seats 206 that prevents excessive penetration by the lower end of the trocar into the interior of the aorta.

Also, because the blades 146 produce a cut in the aorta wall of slightly smaller lateral extent than the outside diameter of the lower portion 110 of the shell 20, a snug fit between the trocar 12 and the aorta wall is created and because closure cap 26 contains a self-sealing septum seal through which the blade assembly 144 passes, blood flow through the trocar from the incised opening in the aorta wall is contained.

Following this, the applicator cover 170 is removed, as shown in FIG. 22, to expose the rear end of the blade assembly 144, particularly the operating heads 152, 162 and 166 of the blade support rod 148, sheath 156 and carrier sleeve 164, respectively. With the support rod head 152 being held against retrograde movement, the head 162 on sheath 156 is pulled upwardly to angularly constrict the blades 146. When the head 162 abuts the spacer flange 154 on the support rod 148 the blades 146 have been completely constricted and moved into the containment slots 168 in the carrier sleeve 164. Next, the carrier sleeve 164 is withdrawn from the trocar 12' by pulling on the head 166 thereof.

An indicating mark (not shown) is provided on the exterior of the carrier sleeve 164 and so positioned thereon as to indicate, when it appears immediately above the spacer 180, that the lower end of the blade assembly 144 is above the valve 140. At this instant the valve operator knob 142 is rotated to close the valve and, thereafter, the spacer 180 and closure cap 26' may be removed from the upper end of the trocar 12'.

When the upper end of the trocar is effectively open upon removal of cap 26', the valve 140 may be opened briefly in order to back bleed the aorta and expel any air that may be entrained in the trocar. Upon again closing the valve 140 the flow line 136 from the heart-lung machine is attached to the trocar by making the connection with the connecting elements 138.

Once the heart-lung machine is functional, blood is circulated through the flow line 136 and trocar internal passage 132 for discharge from the trocar through the opening 134 on the distal side of the shell. Thereafter, inflating fluid in the form of pressurized saline liquid is admitted simultaneously to the pressurizing belt cuff 96' and to the occluder diaphragm 54 by actuation of control valve 129. The flow of inflating liquid through the trocar 12' occurs in series through the inlet connection 128, internal conductor 130, manifold 58', conductors 56' and openings 53 into the interior of the diaphragm 54. Upon inflating, the diaphragm 54 expands laterally, exiting the trocar through the slots 66' whereupon it enters the aortic passage 16 and expands such that the toroidal cushion 62 is brought into occluding engagement with the interior surface of the passage wall. Simultaneous admission of saline liquid to the cuff 96' applies an equal pressure force to the external wall of the aorta in opposition to the force applied by the toroidal cushion 62 of the occluder diaphragm 54 whereby the aortic wall is acted upon by balanced forces to prevent its distention or collapse under the influence of the occluder diaphragm or belt cuff In practice due to the relative flow areas presented to the inflating liquid by the trocar 12' and pressurizing belt 14', respectively, the belt cuff 96' will desirably become pressurized slightly prior in point of time from pressurization of the occluder diaphragm 54.

It will be appreciated that, by so-maintaining the aortic wall, the passage can be effectively occluded without disrupting the wall and without creating the attendant danger of its rupturing or of dislodging material therefrom which could cause serious morbidity or even death to the patient. In occluding the aortic passage its proximal side is rendered quiet and bloodless where the surgery can be performed safely.

Following completion of the surgical procedures requiring occlusion of the aortic passage the diaphragm 54 and cuff 96' are deflated simultaneously by the release of the inflating saline liquid from the interiors of these members by opening valve 129. Desirably a negative pressure may be applied in the fluid line communicating with the manifold 58', conductors 56' and diaphragm interior whereupon the diaphragm is positively induced to collapse so that the trocar 12' can be efficaciously removed from the aorta.

Practice of the invention, furthermore, permits, via a single incision made in the aortic wall, a multitude of ancillary procedures to be performed. For example, by operation of control valve 124 myocardial preservation solution can be periodically admitted to the root of the aorta 16 to arrest and preserve the heart muscle 18 thus to render it quiet and motionless so that cardiac surgery can be performed more effectively. As will be appreciated from consideration of FIG. 17, this is accomplished by the opening of control valve 124 whereby myocardial preservation liquid enters the trocar 12' through inlet connection 118 and flows seriatim through the elbow 120 and passage 42' before exiting the trocar to the proximal side thereof via the discharge opening 48'.

Also, by provision of a fluid line 121 containing control valve 126 communicating with passage 42' via connection 122 and extending to a pressure gauging device (not shown), the pressure in the aorta can be effectively monitored during application of myocardial preservation solution to permit determination of proper and complete distribution of the solution throughout the coronary tree. In addition, when the diaphragm 54 is deflated, this fluid line can be employed to monitor standard systematic pressure.

The fluid passage 42' and opening 48' in the shell wall are further operable for the extraction of fluid from the aorta root and the heart. For example, during the period of aortic occlusion, and when the myocardial preservation solution system is inactive, in order to keep the ascending aorta and heart collapsed and free of blood, a negative pressure can be applied to the passage 42' by appropriate connection of the line 119 to a negative pressure source and the system employed for the removal of blood from the heart and from the aorta root.

Similarly, this same fluid conducting system can also be employed as a means for venting air from the heart and the ascending aorta following completion of the surgical procedure on the heart when the occluding diaphragm 54 has been collapsed so as to remove the flow obstruction from the aortic passage. During this period, when the patient remains on the heart-lung machine and before the blood-ejecting function is returned to the heart, it is necessary to insure that all air bubbles are removed from the heart chambers. This is commonly achieved through use of a vent placed in the left atrium or left ventricle. Upon clamping of this vent to permit filling of the left ventricle and ejection of blood by the heart into the ascending aorta, it is desirable, as an added precaution, to vent an amount of blood from the ascending aorta to insure the evacuation of any micro air bubbles entrained in the blood before they can be dispersed into the cerebral circulation thereby to prevent the danger of possible stroke.

Use of the trocar 12' for the performance of this function is particularly advantageous due in part to the disposition of the opening 48' closely adjacent the upper portion of the aortic wall whereby air can readily migrate into the opening for extraction via passage 42' and the line from connector 119 that, during occlusion of the aorta is used to conduct myocardial solution. Importantly, air extraction in the manner described is enhanced by the protrusion of the trocar 12' into the aorta passage whereby turbulence in the blood flow stream is created. Also, the presence of the deflated diaphragm 54 in the aortic passage creates a restriction tending to retard blood flow and thereby facilitate air removal by enhancing the ability of the air bubbles to migrate to the upper region of the blood flow stream from whence they can be extracted by induction through the opening 48'.

Figure 27:
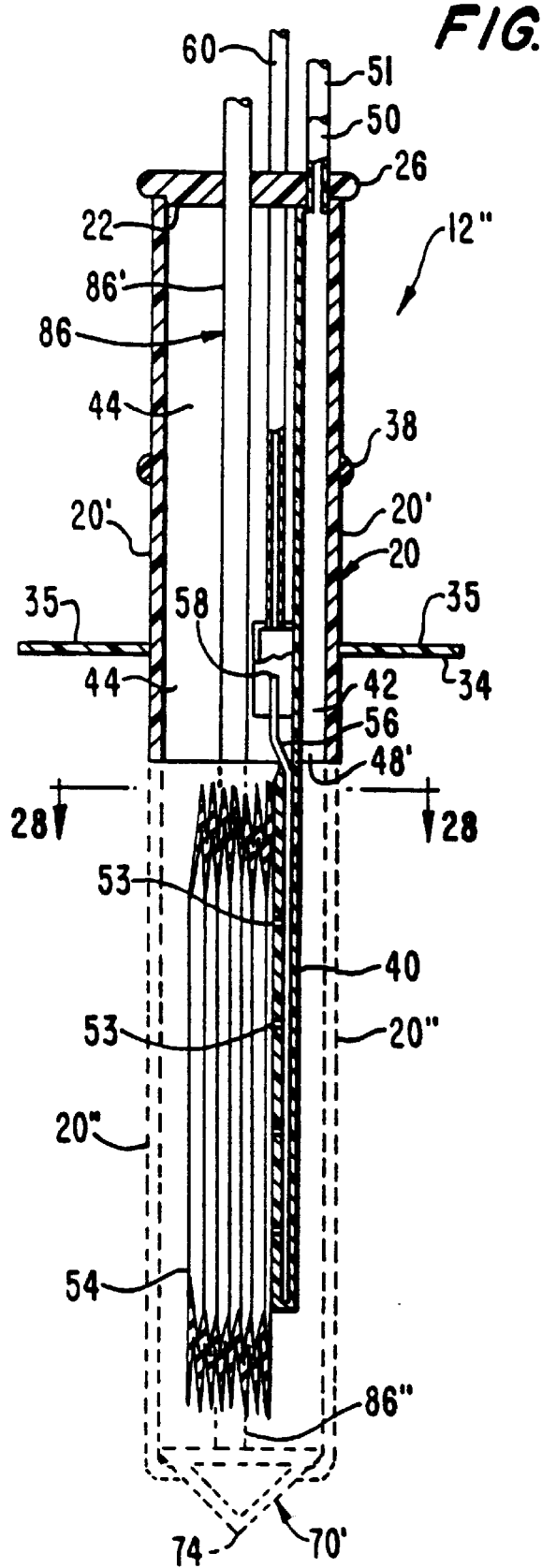
FIG. 27 is a sectional elevational view of a trocar body without the soluble portion of the body carrying an occluding diaphragm in its deflated condition.

The details of construction of a trocar 12" having at least one soluble portion are shown in FIG. 27. Trocar 12" is depicted as comprising an elongated, hollow, substantially cylindrical tubular shell 20 formed of a first portion 20' and a second portion 20", that is open at both its upper and lower ends 22 and 24, respectively. Trocar 12" depicted in FIG. 27 is similar in structure to trocar 12 depicted in FIG. 8, and for clarity of description, similar components are labeled with the same reference numerals. The opening at upper end 22 of shell 20 is closed by a closure cap 26 having openings therein to permit passage of fluid-conducting members, as described above. The opening at lower end 24 of shell 20 is initially of slightly smaller diameter than that of the internal wall surface 28 of the shell, and is defined by an in-turned flange 30 forming a substantially annular shoulder 32 about the opening. Second portion 20" is fabricated of a soluble material and is depicted by dashed lines. When exposed to an appropriate medium, second portion 20" dissolves, thus, changing the size and shape of trocar 12" and leaving only first portion 20'. Soluble portion 20" may be formed on non-soluble portion 20' to form a bond between the portions of shell 20. Alternatively, the portions of shell 20 may be formed separately and joined later by means of a suitable adhesive. Preferably, such an adhesive possesses solubility characteristics similar to those of the material of soluble portion 20", so that the adhesive will not interfere with the insertion or removal of trocar 12" from the vessel or the expansion or collapse of diaphragm 54.

Figure 28:
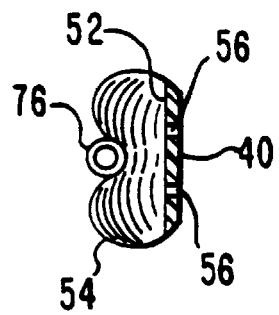
FIG. 28 is a cross-sectional view taken along line 28—28 of FIG. 27.
Figure 29:
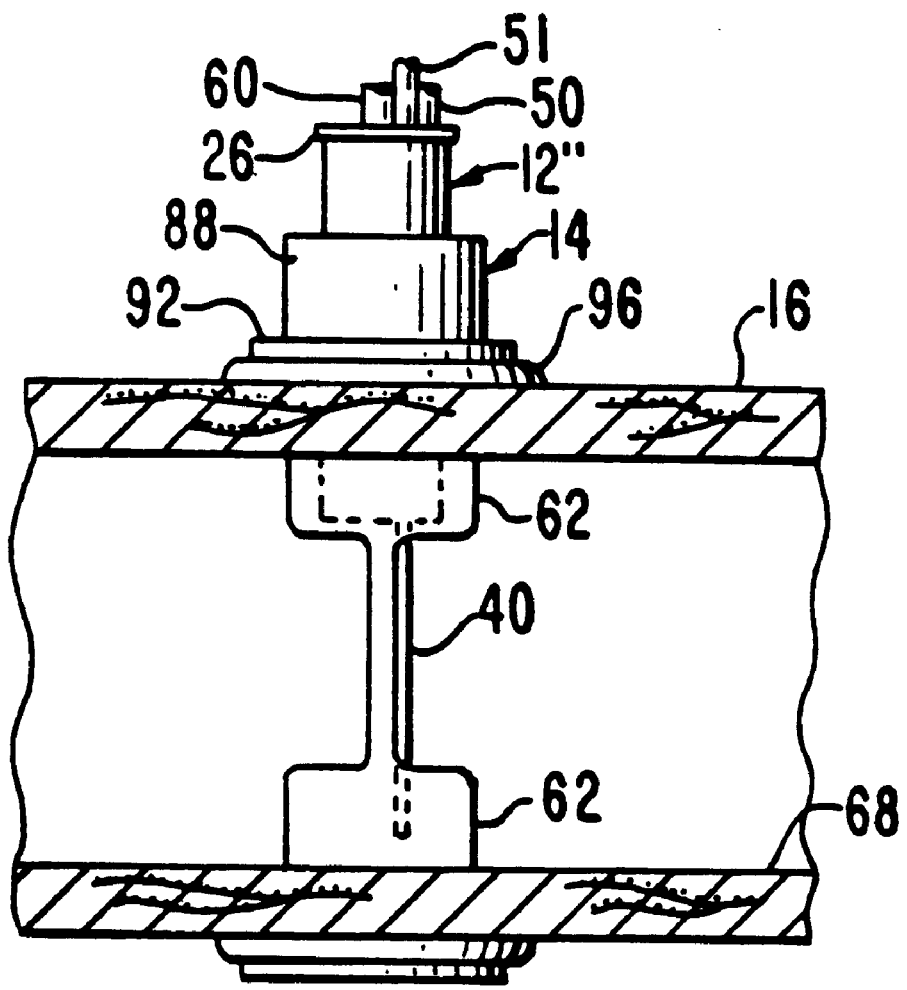
FIG. 29 illustrates the embodiment of FIGS. 27 and 28 when installed in a blood vessel.

Trocar 12" of FIGS. 27–29 may be fabricated of at least two types of materials. First, it may be fabricated of materials that are stable when in contact with a medium and do not dissolve in the range of temperatures of the medium. The non-soluble portion or portions 20' of trocar 12" are fabricated from these materials and form the basic structure for performing the intravascular functions of trocar 12". Second, trocar 12" may be fabricated from materials which, singularly or in combination, are soluble in a medium, such as a water-based medium, e.g., blood. These soluble materials may be organic, e.g. carbohydrates, such as glucose, sucrose, and mannitol; proteins (e.g., albumin); gelatins; plastics; lipids and lipid compounds; polyethyl glycol; or the like. Alternatively, the soluble materials may be inorganic, e.g. sodium chloride, sodium bicarbonate, and the like. Soluble materials also may comprise combinations of these materials.

Suitable materials may have a temperature solubility curve that is intersected at a temperature in a range of about 1° to 41° C. and a solubility rate in a range of about 5 seconds to 30 minutes. Materials used in fabrication of both the first and second portion (or portions) are either biologically inert in the patient's body or readily metabolized by the body and are nontoxic. However, the materials are preferably solid and stable at temperatures below the temperature at the intersection point on the solubility curve.

Soluble portion or portions 20" of trocar 12" may be fabricated as a unitary or a layered solid. Alternatively, the portion or portions may be fabricated in a honeycombed design. Further, a variety of materials with different characteristics may be combined to provide different solubility rates for different purposes. For example, sugar-based materials dissolve more slowly in the medium, such as that described above, than similarly exposed materials including sodium chloride. However, the thickness of such materials may be altered to control the rate at which soluble portion or portions 20" of trocar 12" dissolves (dissolve) in the medium, e.g. in a patient's blood. In a honeycombed design, a soluble, skeletal structure may be fabricated from a strong and rigid material, and honeycombed spaces of this skeletal structure may be filled with sodium chloride or a similar material that quickly dissolves in the medium to provide a larger sugar area allowing the skeletal material to dissolve more rapidly. Moreover, in such a honeycombed design, a substantial portion of soluble trocar portion(s) 20" may comprise the strong and rigid, yet soluble, material, but the honeycomb may have a quick dissolving sodium chloride layer on its surface to provide a smooth surface to facilitate traversing the vessel wall.

As shown in FIGS. 27 and 28 the interior of tubular shell 20 forming trocar 12" is divided longitudinally by a partition plate 40 into transversely spaced regions indicated by the numeral 42 and 44, respectively. The plate 40, as shown in FIG. 28, extends chordally across, the interior of shell 20 and has its opposite side edges sealedly attached to internal wall surface 28. The lower end of partition plate 40 is spaced upwardly from the lower end 24 of the shell 20 and defines region 42 as a fluid conducting passage. A flow opening 48' is an enlarged solitary opening at the lower end of first portion 20' of shell 20 and therethrough, effects fluid communication between the passage 42 and the exterior of trocar 12". A line 50 extends through the closure cap 26 and fluidly connects the other end of the passage 42 to a fluid source, as for example a source of myocardial preservation solution, on the exterior of trocar 12". In one embodiment, line 50 may be fitted with a Y-shaped connection and one branch of this connection may be attached to a source of myocardial preservation solution while the other branch may be connected to a pressure measuring device.

In its expanded condition the diaphragm 54 assumes a shape corresponding essentially to that illustrated in FIG. 29 comprising a generally toroidally-shaped cushion portion 62 and a membrane portion 64 that fills the region of the diaphragm interiorly of the cushion portion. Diaphragm 54 may be inflated with saline solution entering trocar shell 20 through a line 60. The saline solution enters diaphragm 54 through tubes 56 which are contained in plate 40, as shown in FIG. 28. Upon inflation with saline fluid the diaphragm 54 is permitted to expand exteriorly of the trocar 12 by means of a pair of aligned, oppositely spaced slots (not shown) that extend upwardly from the open lower end of the shell 20. Further, these slots may be formed in soluble portion(s) 20" and non-soluble portion 20'. The slots (not shown) are so positioned in the shell 20 with respect to the diaphragm 54 in its deflated condition to enable it to readily project laterally outwardly into engagement with the interior wall 68 of the blood vessel 16. Thus, when expanded, the diaphragm 54 effectively occludes flow through the blood vessel 16 with the opening 48 in shell 20 being disposed in facing relation to the proximal side of the apparatus. Alternatively, however, because portion(s) 20" are soluble, no slots may be necessary to permit release of diaphragm 54. Once portion (s) 20" are dissolved, diaphragm 54 may simply be inflated into engagement with interior wall 68. Because the use of soluble portion(s) 20" eliminates the need for slots (not shown) and the careful alignment of deflated diaphragm 54 with such slots, the cost and complexity of trocar 12" may be significantly reduced.

In addition, as shown in FIG. 29, upon completion of the assembly of a pressurizing belt 14 and trocar 12, a cuff 96 on the belt is disposed on the opposite side of the wall of blood vessel 16 from the occluder cushion 62. In a preferred practice of the invention, the line 60 that supplies saline liquid for expanding the diaphragm 54 is connected in parallel with an inlet 98 to cuff 96 on pressurizing belt 14.

There are several steps in the deployment of an embodiment of the trocar including a medium soluble portion or portions. As with previously described embodiments, first, the trocar is inserted into the vessel, and after insertion, the diaphragm is inflated to perform the trocar's occluding function. In order to avoid damage to the vessel wall and to simplify use, the trocar is shaped to facilitate insertion. In particular, the trocar body may be cylindrical or substantially cylindrical with a smooth outer surface and may include with a tip, such as a cone-shaped or pointed end, to introduce the trocar through the vessel wall.

Referring again to FIG. 27, a rod 86 may extend through trocar 12". Rod 86 may comprise a non-soluble portion 86' and a soluble portion 86". At the lower end of rod 86", trocar 12" may be fitted with a soluble plug 70' having an apex 74 suitable for penetrating the vessel wall. However, once penetration (and insertion) are complete, plug 70' and soluble rod portion 86" are no longer needed and may quickly dissolve in the medium. This structure facilitates the trocar's passage through the vessel wall safely and quickly and without damaging the vessel. Alternatively, rod 86 may be omitted, and soluble plug 70' may be joined to or formed integrally with the lower end of soluble portion 20" of trocar shell 20. For example, plug 70' may be joined to soluble portion 20" by means of a suitable adhesive. Preferably, such an adhesive possesses solublility characteristics similar to those of the material of soluble plug 70' and soluble portion 20". This configuration further simplifies fabrication of trocar 12", and especially, of trocar shell 20, by permitting soluble portion 20" and plug 70' to be fabricated as a single, soluble component.

In addition, once in the vessel, the cylinder shaped trocar body is no longer necessary, and takes up space that could be used to simplify other functions of the trocar. In an embodiment, a substantial portion, e.g. at least about 80%, of the wall forming the cylindrical body may dissolve leaving the non-soluble portion of the trocar extending in a range of about 0.5 cm to 1.5 cm, e.g., about 1.0 cm, into the vessel, the vertical partition, attached catheters, and the occluding balloon. However, the length of the non-soluble portion that extends into the vessel may depend on the diameter of the vessel. The diameter of the vessel may vary with the age, size, and health of the patient, e.g., the presence of plaque on the vessel walls reduces its diameter. To have sufficient strength to form the trocar body, a strong, but soluble, material which is resistant to fragmenting or crumbling, is required, e g.. sugars. Once the trocar is placed, a surgeon might want to use it quickly; however, the soluble portion of the trocar may not dissolve with sufficient speed. Therefore, the soluble portion of the trocar body may be attached to the non-soluble portion of the trocar by means of a quick release portion formed of a rapidly dissolving material, e.g., sodium chloride. This quick release portion may quickly dissolve in the medium and release the soluble portion of the trocar body from the non-soluble portion to allow the inflation of the occluding diaphragm and the use of the cannula and catheters. Such a quick release portion may include a hinged arrangement or a string attachment that would prevent the soluble portion of the trocar body from migrating downstream before it dissolves.

It should be understood that, although preferred embodiments of the invention have been illustrated and described herein, changes and modifications may be made in the described arrangements without departing from the scope of the claims appended hereto.

I claim:

1. A method of cannulating a patient ascending aorta in preparation for surgery, comprising the steps of;

providing an aortic occlusion device having a cutting element, a first lumen, a second lumen and an occluding member, the occluding member being movable from a collapsed condition to an expanded condition;

incising the patient's ascending aorta with the cutting element and inserting the aortic occlusion device into the patient's ascending aorta;

coupling the first lumen to a source of oxygenated blood;

expanding the occluding member to the expanded condition thereby occluding the patient's ascending aorta;

coupling the second lumen to a source of myocardial protection solution;

delivering myocardial protection solution into the patient's ascending aorta through the second lumen; and infusing oxygenated blood into the patient from the source of oxygenated blood.

2. The method of claim 1, wherein:

the delivering step is initiated to arrest the patient's heart.

3. The method of claim 1, further comprising the steps of:

sewing a purse-string suture onto the patient's ascending aorta before the inserting step; and the incising step being carried out by incising the patient's ascending aorta at a location in the purse-string suture.

4. The method of claim 1, wherein:

the providing step is carried out with the cutting element being movable to a position away from the distal end of the aortic occlusion device.

5. A method of cannulating a patient's ascending aorta in preparation for surgery, comprising the steps of:

providing an aortic occlusion device having a tubular body, a stop, a distal end, a first lumen, a second lumen and an occluding member, the occluding member being movable from a collapsed condition to an expanded condition, the stop extending outwardly from the tubular body;

inserting the aortic occlusion device through a penetration in the patient's ascending aorta until the stop contacts the patient's ascending aorta, the tubular body extending from the penetration toward an opposite wall of the patient's ascending aorta;

coupling the first lumen to a source of oxygenated blood;

expanding the occluding member to the expanded condition thereby occluding the patient's ascending aorta;

coupling the second lumen to a source of myocardial protection solution;

delivering myocardial protection solution into the patient's ascending aorta through the second lumen; and infusing oxygenated blood into the patient from the source of oxygenated blood.

6. The method of claim 5, wherein:

the delivering step is initiated to arrest the patient's heart.

7. The method of claim 5, further comprising the steps of:

sewing a purse-string suture onto the patient's ascending aorta before the inserting step; and the inserting step being carried out by inserting the aortic occlusion device through the purse-string suture.

8. The method of claim 5, wherein:

the inserting step is carried out with the distal end of the aortic occlusion device having a conical shape.

9. The method of claim 5, wherein:

the providing step is carried out with the aortic occlusion device having a cutting element at the distal end; and the inserting step being carried out with the cutting element incising the patient's ascending aorta.

10. The method of claim 9, further comprising the step of:

moving the cutting element away from the distal end of the aortic occlusion device.

* * * * *